United States Patent
Riley et al.

(10) Patent No.: US 6,204,259 B1
(45) Date of Patent: Mar. 20, 2001

(54) MANGANESE COMPLEXES OF NITROGEN-CONTAINING MACROCYCLIC LIGANDS EFFECTIVE AS CATALYSTS FOR DISMUTATING SUPEROXIDE

(75) Inventors: Dennis P. Riley, Ballwin; Randy H. Weiss, St. Louis; William L. Neumann, Kirkwood; Anil S. Modak, Maryland Heights; Patrick J. Lennon, Clayton; Karl W. Aston, Pacific, all of MO (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 08/004,444

(22) Filed: Jan. 14, 1993

(51) Int. Cl.$^7$ ................................................ A61K 31/555
(52) U.S. Cl. ........................... 514/184; 514/185; 514/186
(58) Field of Search ................................. 514/184, 185, 514/186

(56) References Cited

U.S. PATENT DOCUMENTS

| | | |
|---|---|---|
| 3,930,867 | 1/1976 | Bigelow. |
| 4,001,212 | 1/1977 | Richman. |
| 4,702,998 | 10/1987 | Tanaka et al.. |
| 4,885,363 | 12/1989 | Tweedle et al.. |
| 5,096,724 | 3/1992 | Zenner et al.. |

FOREIGN PATENT DOCUMENTS

| | | |
|---|---|---|
| 14611 | 10/1988 | (AU). |
| 284645 | 10/1988 | (EP). |
| 287465 | 10/1988 | (EP). |
| 374929 | 6/1990 | (EP). |
| 391766 | 10/1990 | (EP). |
| 436189 | 7/1991 | (EP). |
| WO 12119 | 12/1989 | (WO). |

OTHER PUBLICATIONS

J P 59–193 824–A, Derwent Abstract, Apr. 20, 1983, Japan.*
JP 59–98,074–A, Derwent Abstract, Jun. 6, 1984, Japan.*
Chemical Abstracts 94(24): 197 601s, 1980.*
Chemical Abstracts 102(7): 59159m, 1984.*
Jackels, S.C. et al., "Aqueous Proton NMR Relaxation Enhancement by Manganese (II) Macrocyclic Complexes: Structure–Relaxivity Relationships", *Inorg. Chem.*, 31, 234–39 (1992).
Kimura, E. et al., "Superoxide Dismutase Activity of Macrocyclic Polyamine Complexes", *Biochem.Biophys. Acta*, 678(2), 172–9 (1981).
Newton, J.E. et al., "Synthesis and Characterization of the Mn(II) Complex of [15]aneN$_5$", *J. Coord. Chem.*, vol. 19, pp. 265–277 (1988).
Weiss, R.H. et al., "Catalytic Efficacies of Agents that Dismutate Superoxide", *J. Cell. Biochem.* Suppl. 15C,216, abstract CC110 (1991).
Petkau, A., "Scientific Basis for the Clinical Use of Superoxide Dismutase", *Cancer Treat. Rev.* vol. 13, pp. 17–44 (1986).
McCord, J. M., "Superoxide Dismutase: Rationale for Use in Reperfusion Injury and Inflammation", *J. Free Radicals Biol. Med.* vol. 2, pp. 307–310 (1986).
Bannister, J.V. et al., "Aspects of the Structure, Function, and Applications of Superoxide Dismutase", CRC Crit. Rev. Biochem. vol. 22, (2) pp. 111–180 (1987).
Richman, J. E. et al., "Nitrogen Analogs of Crown Ethers", *J. Am. Chem. Soc.*, vol. 96, (7) pp. 2268–70 (1974).
Atkins, T.J. et al., "Macrocyclic Polyamines: 1,4,7,10,13, 16–Hexaazacyclooctadecane", *Org. Synth.*, vol. 58, pp. 86–98 (1978).
Riley, D.P. et al., "Stopped–Flow Kinetic Analysis for Monitoring Superoxide Decay in Aqueous Systems", *Anal. Biochem.*, vol. 196, pp. 344–349 (1991).
Bull, C. et al., "The Mechanism of Fe–EDTA Catalyzed Superoxide Dismutation", *J. Am. Chem. Soc.*, vol. 105, pp. 5290–5300 (1983).
Kimura, E. et al., "Further Studies on Superoxide Dismutate Activities of Macrocyclic Polyamine Complexes of Copper (II)", *Biochim. Biophys. Acta*, vol. 745, pp. 37–43 (1983).
Rush, J.D. et al., "The Superoxide Dismutase Activities of Two Higher–Valent Manganese Complexes, Mn$^{IV}$ Desferrioxamine and Mn$^{III}$ Cyclam", *Arch. Biochem. Biophys.*, vol. 289, (1) pp. 1–6 (1991).

(List continued on next page.)

*Primary Examiner*—Minna Moezie
*Assistant Examiner*—S. Wang
(74) *Attorney, Agent, or Firm*—Senniger, Powers, Leavitt & Roedel

(57) ABSTRACT

The present invention is directed to low molecular weight mimics of superoxide dismutase (SOD) represented by the formula:

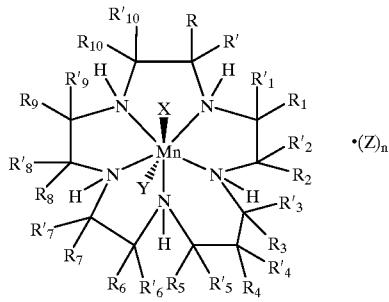

wherein R, R', R$_1$, R'$_1$, R$_2$, R'$_2$, R$_3$, R'$_3$, R$_4$, R'$_4$, R$_5$, R'$_5$, R$_6$, R'$_6$, R$_7$, R'$_7$, R$_8$, R'$_8$, R$_9$, R'$_{10}$, R$_{10}$ and R'$_{10}$, X, Y, Z and n are as defined herein, useful as therapeutic agents for inflammatory disease states and disorders, ischemic/reperfusion injury, myocardial infarction, stroke, atherosclerosis, and all other conditions of oxidant-induced tissue damage or injury.

7 Claims, No Drawings

OTHER PUBLICATIONS

Fretland, D. J. et al., "Superoxide Dismutase (SOD) Modulates Acetic Acid–Induced Colitis in Rodents", *Gastroenterology*, vol. 100, p. A581 (1990).

Gryglewski, R. J. et al., "Superoxide Anion is Involved in the Breakdown of Endothelium–Derived Vascular Relaxing Factor", *Nature*, vol. 320, pp. 454–456 (1986).

Alexander, M.D., "Manganese (II) Complexes of a Macrocyclic Ligand", *Inorg. Nucl. Chem. Letters*, vol. 6, pp. 445–448 (1970).

Brady, S.F. et al., "Practical Synthesis of Cyclic Peptides, with an Example of Dependence of Cyclization Yield upon Linear Sequence", *J. Org. Chem.*, vol. 44, pp. 3101–3105 (1979).

Tabushi, I. et al., "Preparation of C–Alkylated Macrocyclic Polyamines", *Tetrahedron Letters*, No. 12, pp. 1049–52 (1977).

Fujioka, H. et al., "The Effects of Size and donor Atoms of Macrocyclic Polyamines Binding to $Mg^{2+}$ and $Ca^{2+}$", *Chem. Letters*, pp. 737–740 (1982).

Krakowiak, K.E. et al., "Preparation of Triaza–, Tetraaza– and Peraza– Crown Compounds Containing Aminoalkyl Side Groups or Unsubstituted Ring Nitrogen Atoms", *J. Org. Chem.*, vol. 55, pp. 3364–3368 (1990).

Bradshaw, J.S. et al., "A Simple Crab–Like Cyclization Procedure to Prepare Polyaza–Crowns and Cyclams With One or Two Unsubstituted Macroring Nitrogen Atoms or With a Hydroxy Group", *J. Heterocyclic Chem.*, vol. 26, pp. 1431–35 (1989).

Krakowiak, K.E. et al., "Novel Syntheses of Monofunctionalized Triaza–Crowns and Cyclams With a Secondary Amine Group on a Side Chain", *Tetrahedron Letters*, vol. 30, No. 22, pp. 2897–2900 (1989).

Krakowiak, K.E. et al., "Preparation and Strucutal Properties of Large–Cavity Peraza Macrocycles Containing Pyridine, Phenanthroline or Piperazine Subcyclic Units", *J. Org. Chem.*, vol. 56, pp. 2675–80 (1991).

\* cited by examiner

MANGANESE COMPLEXES OF NITROGEN-CONTAINING MACROCYCLIC LIGANDS EFFECTIVE AS CATALYSTS FOR DISMUTATING SUPEROXIDE

BACKGROUND OF THE INVENTION

1. Field of the Invention

The present invention relates to compounds effective as catalysts for dismutating superoxide and, more particularly, relates to manganese(II) or manganese(III) complexes of nitrogen-containing sixteen-membered macrocyclic ligands which catalytically dismutate superoxide.

2. Related Art

The enzyme superoxide dismutase catalyzes the conversion of superoxide into oxygen and hydrogen peroxide according to equation (1) (hereinafter referred to as dismutation). Reactive oxygen metabolites derived from superoxide are postulated to contribute to the tissue pathology in a number of $$O_2^{\cdot-} + O_2^{\cdot-} + 2H^+ \rightarrow O_2 + H_2O_2 \qquad (1)$$

inflammatory diseases and disorders, such as reperfusion injury to the ischemic myocardium, inflammatory bowel disease, rheumatoid arthritis, osteoarthritis, atherosclerosis, hypertension, metastasis, psoriasis, organ transplant rejections, radiation-induced injury, asthma, influenza, stroke, burns and trauma. See, for example, Simic, M. G., et al, Oxygen Radicals in Biology and Medicine, Basic Life Sciences, Vol. 49, Plenum Press, New York and London, 1988; Weiss J. Cell. Biochem., 1991 Suppl. 15C, 216 Abstract C110 (1991); Petkau, A., Cancer Treat. Rev. 13, 17 (1986); McCord, J. Free Radicals Biol. Med., 2, 307 (1986); and Bannister, J. V. et al, Crit. Rev. Biochem., 22, 111 (1987).

It is also known that superoxide is involved in the breakdown of endothelium-derived vascular relaxing factor (EDRF), which has been identified as nitric oxide (NO), and that EDRF is protected from breakdown by superoxide dismutase. This suggests a central role for activated oxygen species derived from superoxide in the pathogenesis of vasospasm, thrombosis and atherosclerosis. See, for example, Gryglewski, R. J. et al., "Superoxide Anion is Involved in the Breakdown of Endothelium-derived Vascular Relaxing Factor", Nature, Vol. 320, pp. 454–56 (1986) and Palmer, R. M. J. et al., "Nitric Oxide Release Accounts for the Biological Activity of Endothelium Derived Relaxing Factor", Nature, Vol. 327, pp. 523–26 (1987).

Clinical trials and animal studies with natural, recombinant and modified superoxide dismutase enzymes have been completed or are ongoing to demonstrate the therapeutic efficacy of reducing superoxide levels in the disease states noted above. However, numerous problems have arisen with the use of the enzymes as potential therapeutic agents, including lack of oral activity, short half-lives in vivo, immunogenicity with nonhuman derived enzymes, and poor tissue distribution.

SUMMARY OF THE INVENTION

The present invention is directed to low molecular weight mimics of superoxide dismutase (SOD) useful as therapeutic agents for inflammatory disease states and disorders which are mediated, at least in part, by superoxide. The SOD mimics of the present invention are manganese(II) or manganese(III) complexes of nitrogen-containing sixteen-membered macrocyclic ligands.

DETAILED DESCRIPTION OF THE INVENTION

The present invention is directed to manganese(II) or manganese(III) complexes of nitrogen-containing sixteen-membered macrocyclic ligands which catalyze the conversion of superoxide into oxygen and hydrogen peroxide. These complexes can be represented by the formula:

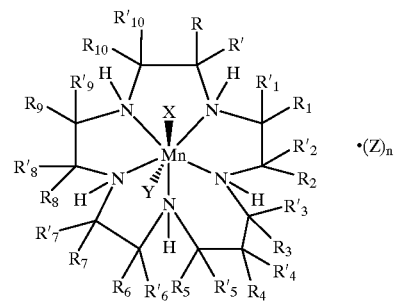

wherein R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$ and $R'_{10}$ independently represents hydrogen, alkyl, alkenyl, alkynyl, cycloalkyl, cycloalkenyl, cycloalkylalkyl, cycloalkylcycloalkyl, cycloalkenylalkyl, alkylcycloalkyl, alkylcycloalkenyl, alkenylcycloalkyl, alkenylcycloalkenyl, heterocyclic, aryl and aralkyl radicals; $R_1$ or $R'_1$ and $R_2$ or $R'_2$, $R_3$ or $R'_3$ and $R_4$ or $R'_4$, $R_3$ or $R'_3$ and $R_5$ or $R'_5$, $R_4$ or $R'_4$ and R or $R'_5$, $R_6$ or $R'_6$ and $R_7$ or $R'_7$, $R_8$ or $R'_8$ and $R_9$ or $R'_9$, and $R_{10}$ or $R'_{10}$ and R or R' together with the carbon atoms to which they are attached independently form a saturated, partially saturated or unsaturated cyclic having 3 to 20 carbon atoms; R or R' and $R_1$ or $R'_1$, $R_2$ or $R'_2$ and $R_3$ or $R'_3$ or $R_4$ or $R'_4$, $R_4$ or $R'_4$ or R or $R'_5$ and $R_6$ or $R'_6$, $R_7$ or $R'_7$ and $R_8$ or $R'_8$, and $R_9$ or $R'_9$ and $R_{10}$ or $R'_{10}$ together with the carbon atoms to which they are attached independently form a nitrogen containing heterocycle having 2 to 20 carbon atoms provided that when the nitrogen containing heterocycle is an aromatic heterocycle which does not contain a hydrogen attached to the nitrogen, the hydrogen attached to the nitrogen as shown in the above formula, which nitrogen is also in the macrocyclic ligand or complex, and the R groups attached to the same carbon atoms of the macrocycle are absent; R and R', $R_1$ and $R'_1$, $R_2$ and $R'_2$, $R_3$ and $R'_3$, $R_4$ and $R'_4$, R and $R'_5$, $R_6$ and $R'_6$, $R_7$ and $R'_7$, $R_8$ and $R'_8$, $R_9$ and $R'_9$, and $R_{10}$ and $R'_{10}$ together with the carbon atom to which they are attached independently form a saturated, partially saturated, or unsaturated ring structure having 3 to 20 carbon atoms; and one of R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$ and $R'_{10}$ together with a different one of R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$ and $R'_{10}$ which is attached to a different carbon atom in the macrocyclic ligand may be bound to form a strap represented by the formula

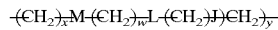

wherein w, x, y and z independently are integers from 0 to 10 and M, L and J are independently selected from the group consisting of alkyl, alkenyl, alkynyl, aryl, cycloalkyl, heteroaryl, alkaryl, alkheteroaryl, aza, amide, ammonium, oxa, thia, sulfonyl, sulfinyl, sulfonamide, phosphoryl, phosphinyl, phosphino, phosphonium, keto, ester, carbamate, urea, thiocarbonyl, borates, boranes, boraza, silyl, siloxy, silaza and combinations thereof; and combinations thereof. Thus, the complexes of the present invention can have any combinations of R groups, saturated, partially saturated or unsaturated cyclics, nitrogen containing heterocycles, saturated, partially saturated or unsaturated ring structures and straps as defined above.

The "R" groups attached to the carbon atoms of the macrocycle can be in the axial or equatorial position relative to the macrocycle. When the "R" group is other than hydrogen or when two adjacent "R" groups, i.e., on adjacent carbon atoms, together with the carbon atoms to which they are attached form a saturated, partially saturated or unsaturated cyclic or a nitrogen containing heterocycle, or when two R groups on the same carbon atom together with the carbon atom to which they are attached form a saturated, partially saturated or unsaturated ring structure, it is preferred that at least some of the "R" groups are in the equatorial position for reasons of improved activity and stability. This is particularly true when the complex contains more than one "R" group which is not hydrogen.

X, Y and Z represent suitable ligands or charge-neutralizing anions which are derived from any monodentate or polydentate coordinating ligand or ligand system or the corresponding anion thereof (for example benzoic acid or benzoate anion, phenol or phenoxide anion, alcohol or alkoxide anion). X, Y and Z are independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid (such as acetic acid, trifluoroacetic acid, oxalic acid), aryl carboxylic acid (such as benzoic acid, phthalic acid), urea, alkyl urea, aryl urea, alkyl aryl urea, thiourea, alkyl thiourea, aryl thiourea,alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate aryl thiocarbamate, alkyl aryl thiocarbamate, alkyl dithiocarbamate, aryl dithiocarbamate, alkyl aryl dithiocarbamate, bicarbonate, carbonate, perchlorate, chlorate, chlorite, hypochlorite, perbromate, bromate, bromite, hypobromite, tetrahalomanganate, tetrafluoroborate, hexafluorophosphate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or systems where one or more of X, Y and Z are independently attached to one or more of the "R" groups, wherein n is an integer from 0 to 3. The preferred ligands from which X, Y and Z are selected include halide, organic acid, nitrate and bicarbonate anions.

Currently, preferred compounds are those wherein at least one, preferably at least two, of the "R" groups represent alkyl, cycloalkylalkyl, aralkyl, aminoalkyl and o-hydroxybenzyl radicals and the remaining R groups represent hydrogen, a saturated, partially saturated or unsaturated cyclic, or a nitrogen containing heterocycle, those wherein at least one, preferably at least two, of $R_1$ or $R'_1$ and $R_2$ or $R'_2$, $R_3$ or $R'_3$ and $R_4$ or $R'_4$, $R_3$ or $R'_3$ and $R_5$ or $R'_5$, $R_4$ or $R'_4$ and R or $R'_5$, $R_6$ or $R'_6$ and $R_7$ or $R'_7$, or $R'_8$ and $R_9$ or $R'_9$, and $R_{10}$ or $R'_{10}$ and R or R' together with the carbon atoms to which they are attached represent a saturated, partially saturated or unsaturated cyclic having 3 to 20 carbon atoms and all the remaining "R" groups are hydrogen, nitrogen containing heterocycle or alkyl groups, and those wherein at least one, preferably at least two, of R or R' and $R_1$ or $R'_1$, $R_2$ or $R'_2$ and $R_3$ or $R'_3$ or $R_4$ or $R'_4$, $R_4$ or $R'_4$ or R or $R'_5$ and $R_6$ or $R'_6$, $R_7$ or $R'_7$ and $R_8$ or $R'_8$, and $R_9$ or $R'_9$ and $R_{10}$ or $R'_{10}$ together with the carbon atoms to which they are attached are bound to form a nitrogen containing heterocycle having 2 to 20 carbon atoms and all the remaining "R" groups are independently selected from hydrogen, saturated, partially saturated or unsaturated cyclic or alkyl groups. As used herein, "R" groups means all of the R groups attached to the carbon atoms of the macrocycle, i.e., R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$ and $R'_{10}$.

The commonly accepted mechanism of action of the manganese-based SOD enzymes involves the cycling of the manganese center between the two oxidation states (II,III). See J. V. Bannister, W. H. Bannister, and G. Rotilio, Crit. Rev. Biochem., 22, 111–180 (1987).

$$Mn(II)+HO_2 \rightarrow Mn(III)+HO_2 \qquad 1)$$

$$Mn(III)+O_2^{\cdot -} \rightarrow Mn(II)+O_2 \qquad 2)$$

The formal redox potentials for the $O_2/O_2^{\cdot -}$ and $HO_2/H_2O_2$ couples at pH=7 are −0.33 v and 0.87 v, respectively. See A. E. G. Cass, in Metalloproteins: Part 1, Metal Proteins with Redox Roles, ed. P. Harrison, P. 121. Verlag Chemie (Weinheim, GDR) (1985). For the above disclosed mechanism, these potentials require that a putative SOD catalyst be able to rapidly undergo oxidation state changes in the range of about −0.33 v to about 0.87 v.

The complexes derived from Mn(II) and the general class of C-substituted [16]aneN$_5$ ligands described herein have been characterized using cyclic voltammetry to measure their redox potential. The C-substituted complexes described herein have oxidations of about +0.7 v (SHE). Coulometry shows that this oxidation is a one-electron process; namely it is the oxidation of the Mn(II) complex to the Mn(III) complex. Thus, for these complexes to function as SOD catalysts, the Mn(III) oxidation state is involved in the catalytic cycle. This means that the Mn(III) complexes of all these ligands are equally competent as SOD catalysts, since it does not matter which form (Mn(II) or Mn(III)) is present when superoxide is present because superoxide will simply reduce Mn(III) to Mn(II) liberating oxygen.

As utilized herein, the term "alkyl", alone or in combination, means a straight-chain or branched-chain alkyl radical containing from 1 to about 22 carbon atoms, preferably from about 1 to about 18 carbon atoms, and most preferably from about 1 to about 12 carbon atoms. Examples of such radicals include, but are not limited to, methyl, ethyl, n-propyl, isopropyl, n-butyl, isobutyl, sec-butyl, tert-butyl, pentyl, iso-amyl, hexyl, octyl, nonyl, decyl, dodecyl, tetradecyl, hexadecyl, octadecyl and eicosyl. The term "alkenyl", alone or in combination, means an alkyl radical having one or more double bonds. Examples of such alkenyl radicals include, but are not limited to, ethenyl, propenyl, 1-butenyl, cis-2-butenyl, trans-2-butenyl, iso-butylenyl, cis-2-pentenyl, trans-2-pentenyl, 3-methyl-1-butenyl, 2,3-dimethyl-2-butenyl, 1-pentenyl, 1-hexenyl, 1-octenyl, decenyl, dodecenyl, tetradecenyl, hexadecenyl, cis- and trans-9-octadecenyl, 1,3-pentadienyl, 2,4-pentadienyl, 2,3-pentadienyl, 1,3-hexadienyl, 2,4-hexadienyl, 5,8,11,14-eicosatetraenyl, and 9,12,15-octadecatrienyl. The term "alkynyl", alone or in combination, means an alkyl radical having one or more triple bonds. Examples of such alkynyl groups include, but are not limited to, ethynyl, propynyl (propargyl), 1-butynyl, 1-octynyl, 9-octadecynyl, 1,3-pentadiynyl, 2,4-pentadiynyl, 1,3-hexadiynyl, and 2,4-hexadiynyl. The term "cycloalkyl", alone or in combination means a cycloalkyl radical containing from 3 to about 10, preferably from 3 to about 8, and most preferably from 3 to about 6, carbon atoms. Examples of such cycloalkyl radicals include, but are not limited to, cyclopropyl, cyclobutyl, cyclopentyl, cyclohexyl, cycloheptyl, cyclooctyl, and perhydronaphthyl. The term "cycloalkylalkyl" means an alkyl radical as defined above which is substituted by a cycloalkyl radical as defined above. Examples of cycloalkylalkyl radicals include, but are not limited to, cyclohexylmethyl, cyclopentylmethyl, (4-isopropylcyclohexyl)methyl, (4-t-butylcyclohexyl)methyl, 3-cyclohexylpropyl, 2-cyclohexylmethylpentyl, 3-cyclopentylmethylhexyl, 1-(4-neopentylcyclohexyl)methylhexyl, and 1-(4-isopropylcyclohexyl)methylheptyl. The term "cycloalkylcycloalkyl" means a cycloalkyl radical as defined above which is substituted by another cycloalkyl radical as defined above. Examples of cycloalkylcycloalkyl radicals include, but are not limited to, cyclohexylcyclopentyl and cyclohexylcyclohexyl. The term "cycloalkenyl", alone or in combination, means a cycloalkyl radical having one or more double bonds. Examples of cycloalkenyl radicals include, but are not limited to, cyclopentenyl, cyclohexenyl, cyclooctenyl, cyclopentadienyl, cyclohexadienyl and cyclooctadienyl. The term "cycloalkenylalkyl" means an alkyl radical as defined above which is substituted by a cycloalkenyl radical as defined above. Examples of cycloalkenylalkyl radicals include, but are not limited to, 2-cyclohexen-1-ylmethyl, 1-cyclopenten-1-ylmethyl, 2-(l-cyclohexen-1-yl)ethyl, 3-(1-cyclopenten-1-yl)propyl, 1-(1-cyclohexen-1-ylmethyl) pentyl, 1-(1-cyclopenten-1-yl)hexyl, 6-(1-cyclohexen-1-yl) hexyl, 1-(1-cyclopenten-1-yl)nonyl and 1-(1-cyclohexen-1-yl)nonyl. The terms "alkylcycloalkyl" and "alkenylcycloalkyl" mean a cycloalkyl radical as defined above which is substituted by an alkyl or alkenyl radical as defined above. Examples of alkylcycloalkyl and alkenylcycloalkyl radicals include, but are not limited to, 2-ethylcyclobutyl, 1-methylcyclopentyl, 1-hexylcyclopentyl, 1-methylcyclohexyl, 1-(9-octadecenyl) cyclopentyl and 1-(9-octadecenyl)cyclohexyl. The terms "alkylcycloalkenyl" and "alkenylcycloalkenyl" means a cycloalkenyl radical as defined above which is substituted by an alkyl or alkenyl radical as defined above. Examples of alkylcycloalkenyl and alkenylcycloalkenyl radicals include, but are not limited to, 1-methyl-2-cyclopentyl, 1-hexyl-2-cyclohexenyl, 1-(9-octadecenyl)-2-cyclohexenyl and 1-(2-pentenyl)-2-cyclohexenyl. The term "aryl", alone or in combination, means a phenyl or naphthyl radical which optionally carries one or more substituents selected from alkyl, cycloalkyl, cycloalkenyl, aryl, heterocycle, alkoxyaryl, alkaryl, alkoxy, halogen, hydroxy, amine, cyano, nitro, alkylthio, phenoxy, ether, trifluoromethyl and the like, such as phenyl, p-tolyl, 4-methoxyphenyl, 4-(tert-butoxy) phenyl, 4-fluorophenyl, 4-chlorophenyl, 4-hydroxyphenyl, 1-naphthyl, 2-naphthyl, and the like. The term "aralkyl", alone or in combination, means an alkyl or cycloalkyl radical as defined above in which one hydrogen atom is replaced by an aryl radical as defined above, such as benzyl, 2-phenylethyl, and the like. The term "heterocyclic" means ring structures containing at least one other kind of atom, in addition to carbon, in the ring. The most common of the other kinds of atoms include nitrogen, oxygen and sulfur. Examples of heterocyclics include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. The term "saturated, partially saturated or unsaturated cyclic" means fused ring structures in which 2 carbons of the ring are also part of the sixteen-membered macrocyclic ligand. The ring structure can contain 3 to 20 carbon atoms, preferably 5 to 10 carbon atoms, and can also contain one or more other kinds of atoms in addition to carbon. The most common of the other kinds of atoms include nitrogen, oxygen and sulfur. The ring structure can also contain more than one ring. The term "saturated, partially saturated or unsaturated ring structure" means a ring structure in which one carbon of the ring is also part of the sixteen-membered macrocyclic ligand. The ring structure can contain 3 to 20, preferably 5 to 10, carbon atoms and can also contain nitrogen, oxygen and/or sulfur atoms. The term "nitrogen containing heterocycle" means ring structures in which 2 carbons and a nitrogen of the ring are also part of the sixteen-membered macrocyclic ligand. The ring structure can contain 2 to 20, preferably 4 to 10, carbon atoms, can be partially or fully unsaturated or saturated and can also contain nitrogen, oxygen and/or sulfur atoms in the portion of the ring which is not also part of the sixteen-membered macrocyclic ligand. The term "organic acid anion" refers to carboxylic acid anions having from about 1 to about 18 carbon atoms. The term "halide" means chloride or bromide. Any of the R groups defined above can optionally carry one or more substituents selected from halogen, amine, hydroxy, cyano, nitro, trifluoromethyl, and the like.

The macrocyclic ligands useful in the complex of the present invention wherein all of the R groups are H can be prepared according to the general synthetic scheme A set forth below utilizing methods known in the art for the preparation of certain intermediates and certain ligands. See for example Richman et al., *J. Am. Chem. Soc.*, 96, 2268, (1974); Atkins et al. *Org. Synth.*, 58, 86 (1978); and EP 287465. Thus in scheme A a tetraazaalkane is tosylated in a suitable solvent system to produce the corresponding tetratosyl derivative. Such derivative is then treated with a suitable base to produce the corresponding disulfonamide anion. This disulfonamide anion is then cycloalkylated with a di-o-tosylated mono-N-tosylated azaalkane diol to produce the pentatosylpentaazacycloalkane. The tosyl groups are then removed and the resulting compound is reacted with a manganese (II) compound under anaerobic conditions to form the corresponding manganese (II) pentaazacycloalkane complex.

The macrocyclic ligands useful in the complexes of the present invention, wherein $R_3$, $R'_3$, $R_4$, $R'_4$, $R_5$ and $R'_5$ can be H or any functionality previously described, can also be prepared according to the general procedure shown in scheme B set forth below. Thus, a 1,3-diaminopropanediamine is converted to its ditosyl derivative in a suitable solvent. This ditosyl derivative is then converted to its disulfonamide anion with a suitable base. Additionally, the triazaalkane is converted to its tritosyl derivative in a similar manner. This tritosyl derivative is then reacted with thylene carbonate and a suitable base to afford the tri-N-tosyl diol derivative. This diol is then converted to the tri-N-tosyl di-O-tosyl derivative in a suitable solvent. The disulfonamide anion is then cycloalkylated with the tri-N-tosyl di-O-tosyl derivative. The tosyl groups are removed and the resulting compound is reacted with a manganese (II) compound under anaerobic conditions to form the corresponding manganese (II) pentaazacycloalkane complex.

The macrocyclic ligands useful in the complexes of the present invention, wherein $R_4$ and $R'_4$ can be H or any functionality previously described and P can be H or tosyl, can be prepared according to scheme C set forth below. The pentaazaalkane is cyclocondensed with a malonyl dichloride or diester in a suitable solvent with a suitable base. The resulting cyclic diamide is then reduced and detosylated to the desired ligand system with lithium aluminum hydride. This type of ligand is then reacted with a manganese (II) compound under anaerobic conditions to afford the corresponding manganese (II) pentaazacycloalkane complex.

The macrocyclic ligands useful in the complexes of the present invention, wherein $R_3$, $R'_3$ and $R_4$ can be H or any functionality previously described and P can be H or tosyl, can be prepared according to scheme D set forth below. The pentaazaalkane is cyclocondensed with an acrylate or acryloyl chloride in a suitable solvent using a suitable base. The resulting cyclic amide is then reduced and detosylated with lithium aluminum hydride. This type of ligand is then reacted with a manganese (II) compound under anaerobic conditions to afford the corresponding manganese (II) pentaazacycloalkane complex.

The macrocyclic ligands containing pendant phenols useful in the complexes of the present invention, wherein $R_3$, $R_4$, $R_{11}$, $R_{12}$, $R_{13}$, and $R_{14}$ can be H or any functionality previously described and P can be H or tosyl, can be prepared according to scheme E set forth below. The pentaazaalkane is cyclocondensed with a coumarin derivative to afford the macrocyclic amide containing a pendant phenol. The resulting cyclic amide is then reduced and detosylated with lithium aluminum hydride. This type of ligand is then reacted with a manganese (II) compound under anaerobic conditions to afford the corresponding manganese (II) pentaazacycloalkane complex.

The macrocyclic ligands useful in the complexes of the present invention can also be prepared according to scheme F, set forth below. The complete possible substitution for Scheme F has been fully illustrated in this method. The other methods (Schemes A through E and G through P) can also have further R substitutions than those shown in the respective methods and such substitutions would be readily apparent to those skilled in the art. Additionally $R_4$ and/or $R'_4$ can be connected to themselves (generating a spiro ring substituent on the trimethylene bridge) and/or any other R group on the macrocyclic ring (R, R', $R_1$, $R'_1$, $R_2$, $R'_2$, $R_6$, $R'_6$, $R_7$, $R'_7$, $R_8$, $R'_8$, $R_9$, $R'_9$, $R_{10}$ and $R'_{10}$) to generate "strapped" macrobicyclic or macrotricyclic ligand systems. In scheme F the pentaazaalkane is cycloalkylated with a 1,3-dihalo or di-o-tosyl propane derivative. The resulting macrocycle is detosylated and reacted with a manganese (II) compound under anaerobic conditions to form the corresponding polysubstituted manganese (II) pentaazacycloalkane complex.

The macrocyclic ligands useful in the complexes of the present invention wherein $R_3$, $R'_3$, $R_4$, $R'_{41}$ $R_5$, and $R'_5$ can be H or any other functionality previously described can also be prepared according to scheme G set forth below. The 1,3-diaminopropane derivative is di-acylated with chloroacetyl chloride. The resulting bis-chloroacetamide is then cycloalkylated with either the triazaalkane or the di-sulfonamide anion of the corresponding tri-N-tosyl triazaalkane. The cyclic diamides are the reduced and detosylated (if necessary) with lithium aluminum hydride. This type of ligand is then reacted with a manganese (II) compound under anaerobic conditions to afford the corresponding manganese (II) pentaazacycloalkane complex.

The macrocyclic ligands useful in the complexes of the present invention wherein $R_3$, $R'_3$, $R_4$, $R'_4$, $R_5$, $R'_5$, R and R' can be H or any other functionality previously described and which also contain a cis- or trans-fused cyclohexyl ring can be prepared according to scheme H set forth below (a system incorporating a trans-fused cyclohexyl ring has been illustrated). The bis-chloroacetamide is cycloalkylated with the triazaalkane or the bis-N-tosyl triazaalkane. The resulting cyclic triamides are then reduced and detosylated (if necessary) with lithium aluminum hydride. This type of ligand is then reacted with a manganese (II) compound under anaerobic conditions to afford the corresponding manganese (II) pentaazacycloalkane complex. The bis-N-tosyl triazaalkane described above can be prepared by monotosylation of diaminocyclohexane followed by coupling with any natural or unnatural amino acid derivative under standard conditions. The Boc group is then removed and the free amine is tosylated. The triazaalkane also described above can be prepared by monosilylation of diaminocyclohexane followed by coupling with any natural or unnatural amino acid derivated under standard conditions. The Boc and the silyl groups can then be removed by treatment with HCl in dioxane followed by free base generation under suitable conditions.

The macrocyclic ligands useful in the complexes of the present invention wherein $R_3$, $R'_3$, $R_4$, and $R'_4$ can be H or any other functionality previously described and which also contain two cis- and/or trans-fused cyclohexyl rings (trans for illustration), can be prepared according to scheme I set forth below. The monosilylated diaminocyclohexane derivative is coupled with any β-amino acid derivative under standard conditions. The Boc and silyl groups are then removed and the resulting triazaalkane is cycloalkylated with the bis-chloroacetamide. The resulting cyclic triamide is then reduced with lithium aluminum hydride. This type of ligand is then reacted with a manganese (II) compound under anaerobic conditions to afford the corresponding manganese (II) pentaazacycloalkane complex containing substitution and two fused cyclohexyl rings.

The macrocyclic ligands useful in the complexes of the present invention wherein $R_4$ and $R'_4$ can be H or any other functionality previously described and two cis- or trans-fused diaminocyclohexane rings (trans for illustration) can be prepared according to scheme J set forth below.

N-tosyliminodiacetic acid is converted to the diacid chloride by reaction with thionyl chloride or oxalyl chloride. The diacid chloride is the reacted with excess diaminocyclohexane to afford the diamino diamide derivative. This derivative is then cyclo-condensed with a malonyl dichloride or diester to afford the macrocyclic tetraamide. This derivative is then reduced and detosylated with lithium aluminum hydride. This type of ligand is reacted with a manganese (II) compound under anaerobic conditions to afford the corresponding manganese (II) pentaazacycloalkane complex containing substitution and two fused cyclohexyl rings.

The macrocyclic ligands useful in the complexes of the present invention wherein $R_1$, $R'_1$, $R_3$, $R'_3$, $R_4$, $R'_4$, $R_6$, $R'_6$, $R_8$, $R'_8$, $R_{10}$ and $R'_{10}$ can be H or any functionality previously described can be prepared according to the general peptide method outlined in scheme K set forth below. The procedures for preparing the cyclic peptide precursors from the corresponding linear peptides are the same or significant modifications of methods known in the art. See, for example, Veber, D. F. et al., *J. Org. Chem.*, 44,3101 (1979) and U.S. patent application Ser. No. 07/902,146. The starting pentapeptide in scheme K can be prepared by standard solution or solid-phase synthesis and must incorporate one β-amino acid. This compound is then converted to the corresponding cyclic peptide by treatment with diphenylphosphoryl azide. The cyclic peptide is then reduced with lithium aluminum hydride. This type of ligand is then reacted with a manganese (II) compound under anaerobic conditions to afford the corresponding manganese (II) pentaazacycloalkane complex.

The macrocyclic ligands useful in the complexes of the present invention wherein $R_1$, $R'_1$, $R_3$, $R'_{31}$ $R_4$, $R'_4$, $R_{10}$ and $R'_{10}$ can be H or any functionality previously described and which also contain one cis- or trans-fused cyclohexane ring can be prepared by scheme L set forth below. Mono-N-tosyl diaminocyclohexane is converted to the Boc derivative under standard conditions. The tosylamide is then alkylated with methyl bromoacetate using a suitable base. The resulting pseudo-dipeptide methyl ester is saponified to the free acid which is coupled with any natural or unnatural amino acid under standard conditions. The Boc group is then removed and the amino group of the pseudo-tripeptide is then coupled to any N-Boc protected β-amino acid derivative under standard conditions. The Boc group is then removed and the free amino group is then coupled to any natural or unnatural amino acid derivative. The resulting pseudo-pentapeptide is then deprotected with HCl/acetic acid and cyclized by treatment with diphenylphosphoryl azide. The cyclic pseudo-peptide is then reduced and detosylated with lithium aluminum hydride. This type of ligand is then reacted with a manganese (II) compound under anaerobic conditions to afford the corresponding manganese (II) pentaazacycloalkane complex containing a fused cyclohexane ring.

The macrocyclic ligands useful in the complexes of the present invention, wherein $R_3$, $R'_3$, $R_4$, and $R'_4$ can be H or any other functionality previously described and which contain two cis- and/or trans-fused cyclohexane ring can be prepared according to scheme M set forth below. The cyclohexyl pseudo-dipeptide is saponified to the free acid. Another amount of the cyclohexyl pseudo-dipeptide is treated with TFA to remove the Boc. These two derivatives are then coupled together under standard conditions. The Boc is then removed from the resulting pseudo-tetrapeptide and the free amino group is coupled to any Boc protected β-amino acid derivative under standard conditions. The pseudo-pentapeptide is then deprotected and cyclized. The cyclic pseudo-peptide is reduced and detosylated with lithium aluminum hydride. This type of ligand is then reacted with a manganese (II) compound under anaerobic conditions to afford the corresponding manganese (II) substituted pentaaza-cycloalkane complex containing two fused cyclohexanes.

The macrocyclic ligands useful in the complexes of the present invention wherein $R_3$, $R'_3$, $R_4$, $R'_4$, $R_5$, $R'_5$, $R_{11}$, $R_{12}$, $R_{13}$ and $R_{14}$ can be H or any functionality previously described and can contain 2-(aminomethyl)cyclohexylamine or 2-(aminomethyl)aniline substitution can be prepared by the general diacid dichloride method previously described and outlined in schemes N, O and P. See, for example, U.S. patent application Ser. No. 07/902, 146 now abandoned, which is incorporated by reference herein. The tri-N-tosyl triazaalkane is alkylated with methyl chloroacetate using a suitable base. The resulting diester is saponified and converted to the diacid chloride under standard conditions. The diacid chloride is then cyclo-condensed with the 1,3-diamine using a suitable solvent and base. The resulting macrocyclic diamide is reduced and detosylated with lithium aluminum hydride. This type of ligand is then reacted with a manganese (II) compound under anaerobic conditions to afford the corresponding manganese (II) pentaazacycloalkane complex.

Scheme A

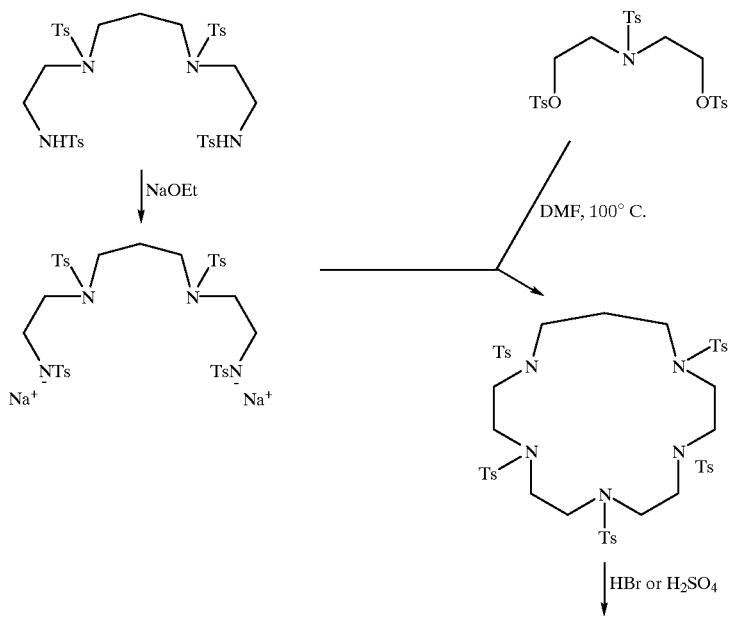
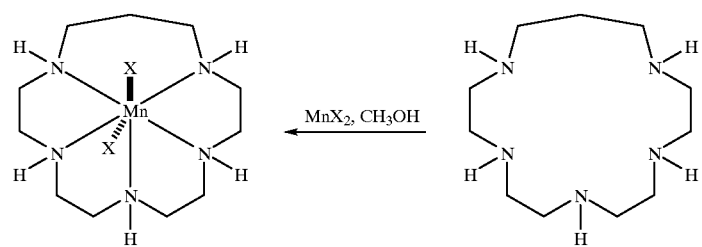
Scheme B
(General Substituted 1,3-propane diamines)
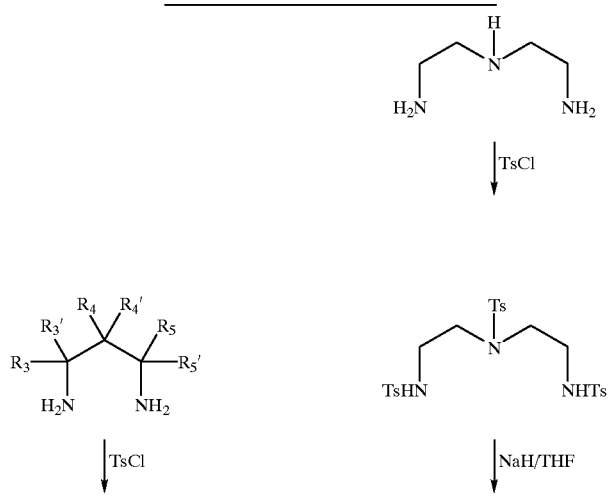

-continued
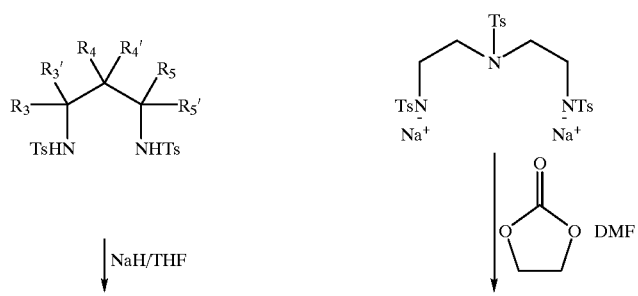
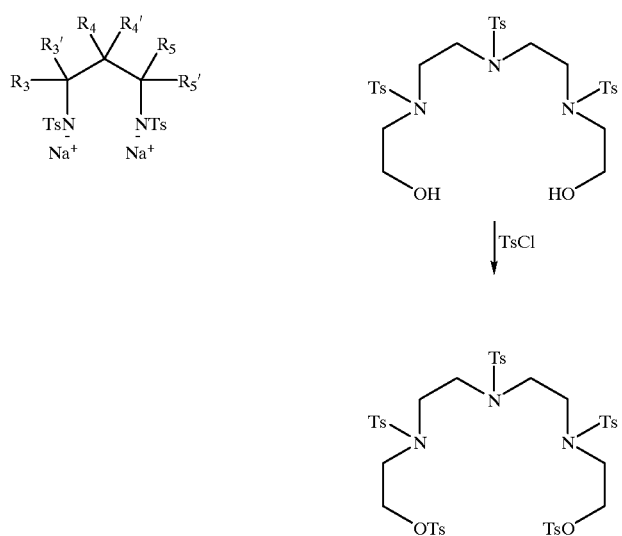
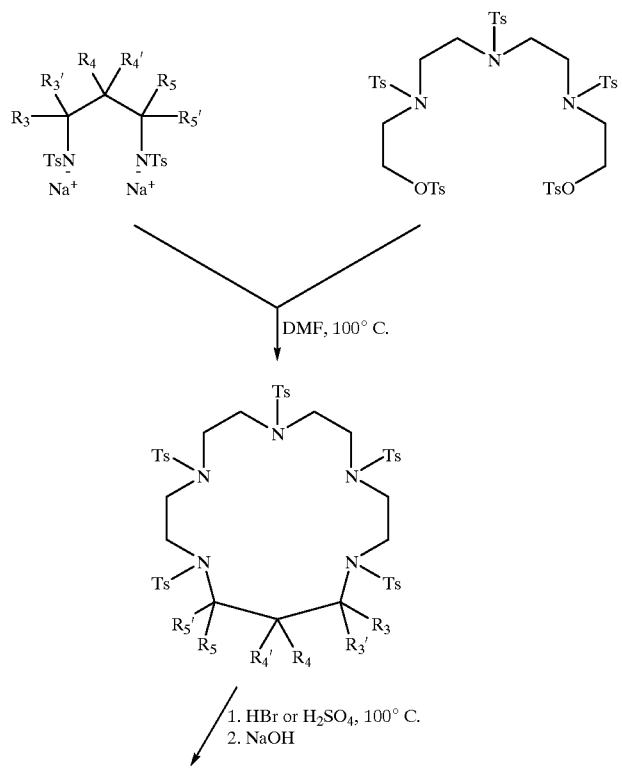

-continued
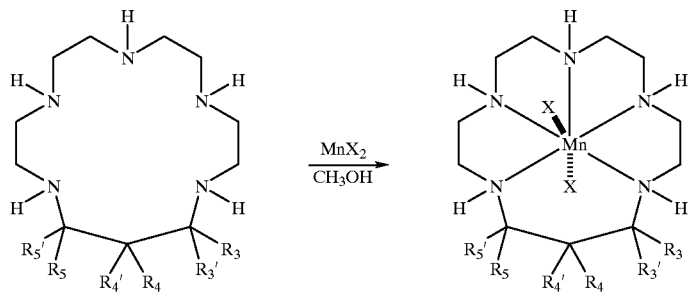
Scheme C
(Malonates)
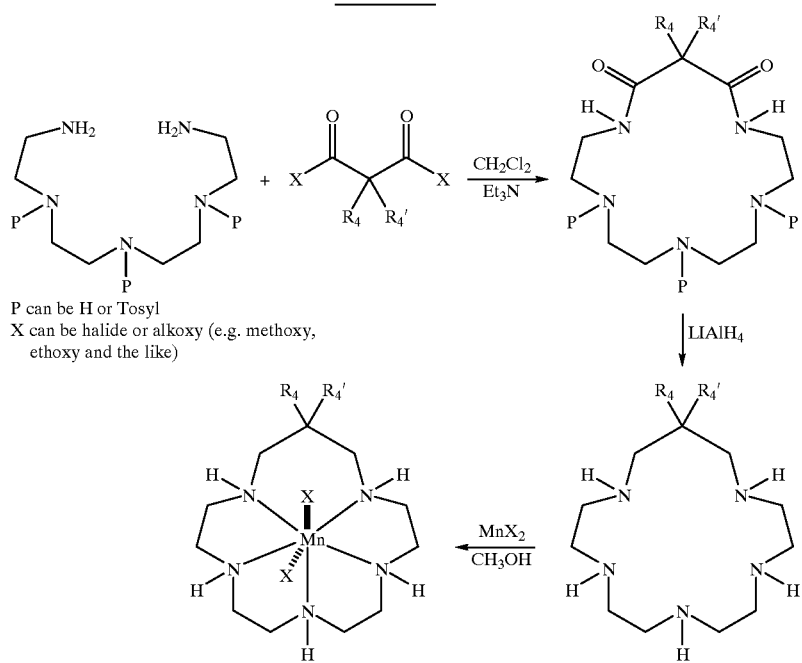
P can be H or Tosyl
X can be halide or alkoxy (e.g. methoxy, ethoxy and the like)
Scheme D
(Acrylates)
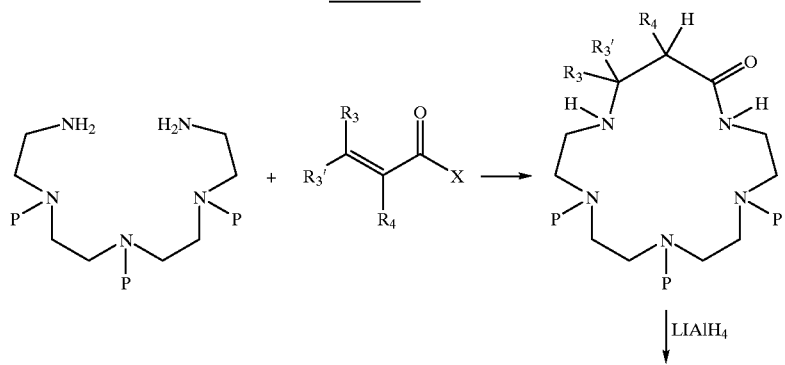

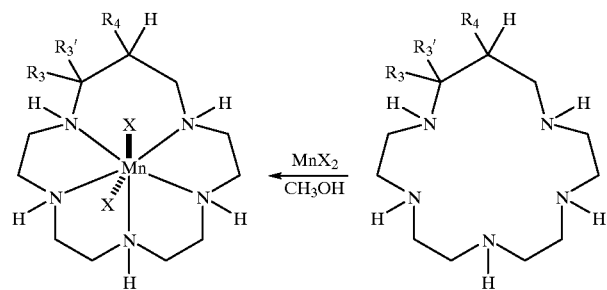
Scheme 3
(Coumarins)
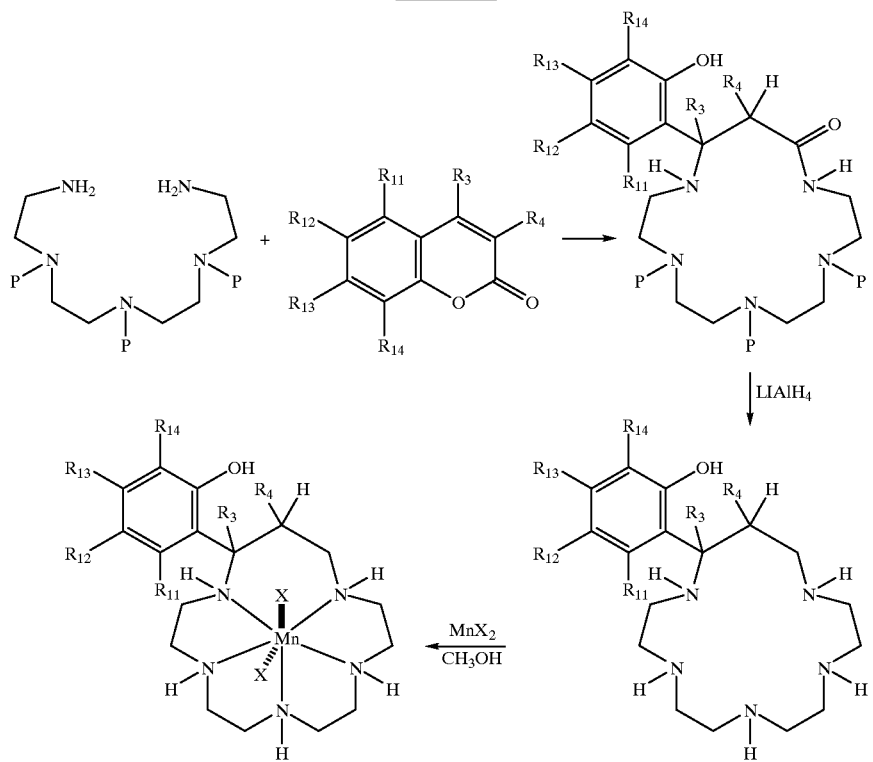
Scheme F
(Alkylations)
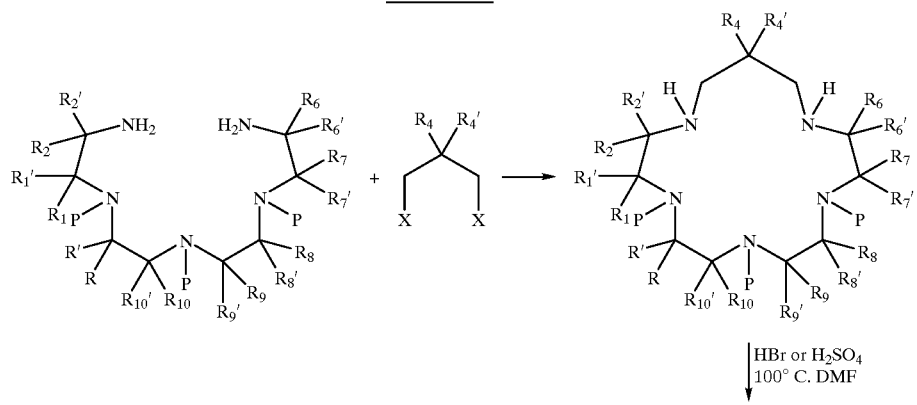

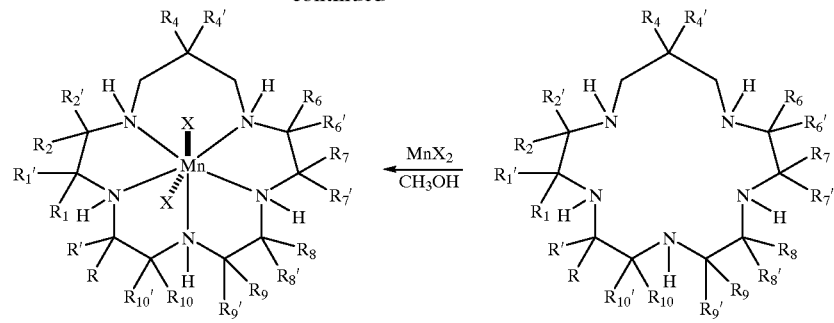
Additionally $R_4$ and/or $R'_4$ can be connected to themselves (generating a spiro ring system on the trimethylene bridge) and/or any other R group on the ring ($R$, $R'$, $R_1$, $R'_1$, $R_2$, $R'_2$, $R_6$, $R'_6$, $R_7$, $R'_7$, $R_8$, $R'_8$, $R_9$, $R'_9$, $R_{10}$ and $R'_{10}$) to generate "strapped" macrobicyclic or macrotricyclic ligand systems.
Scheme G
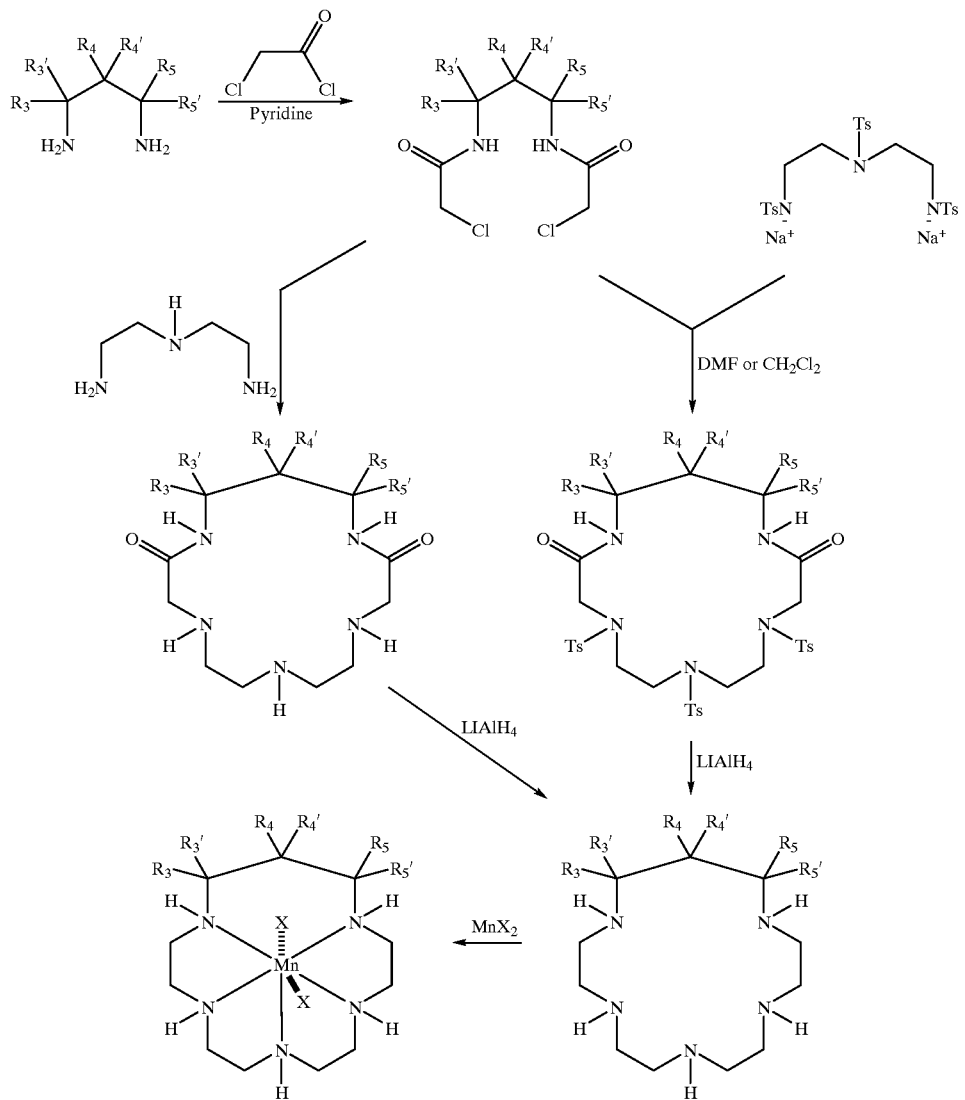

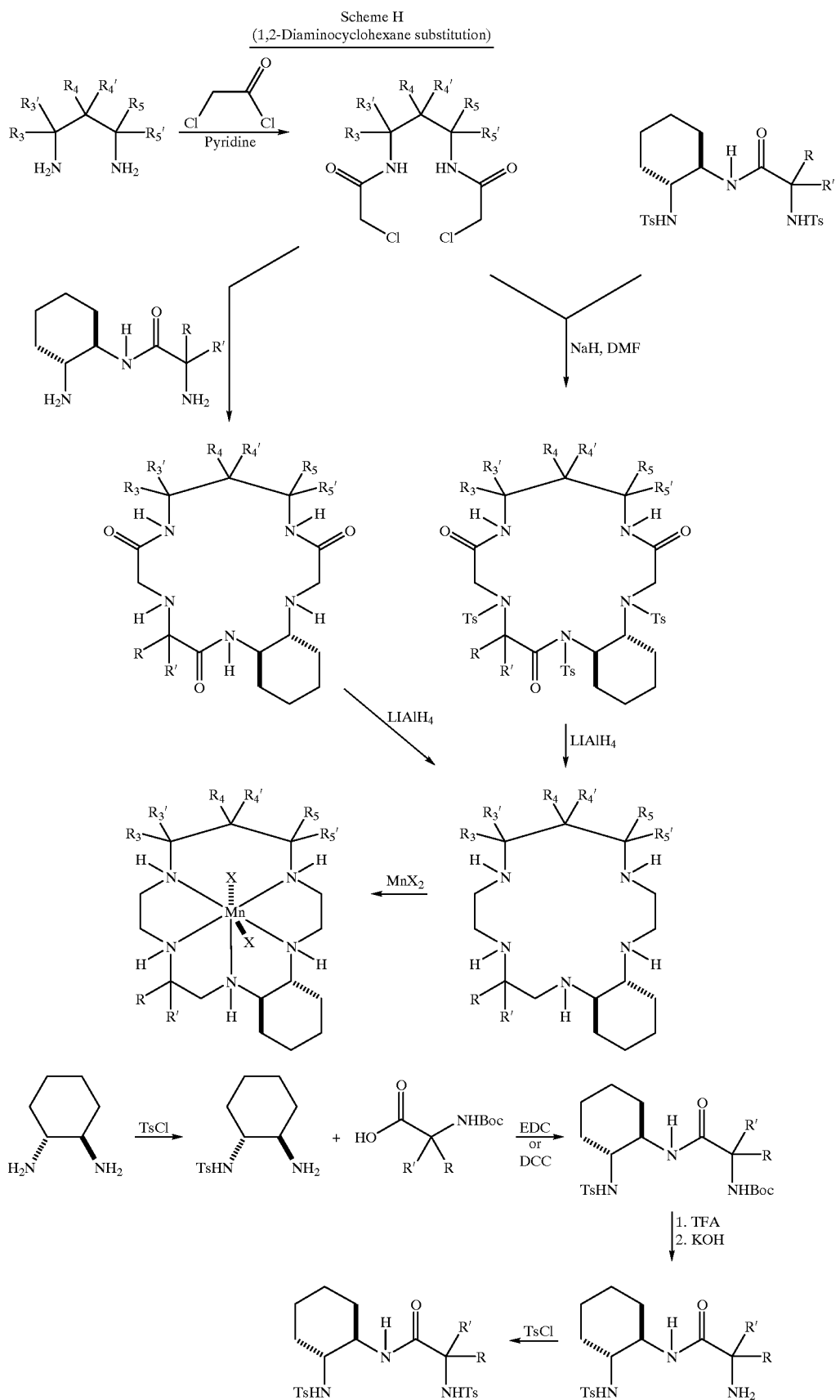

-continued
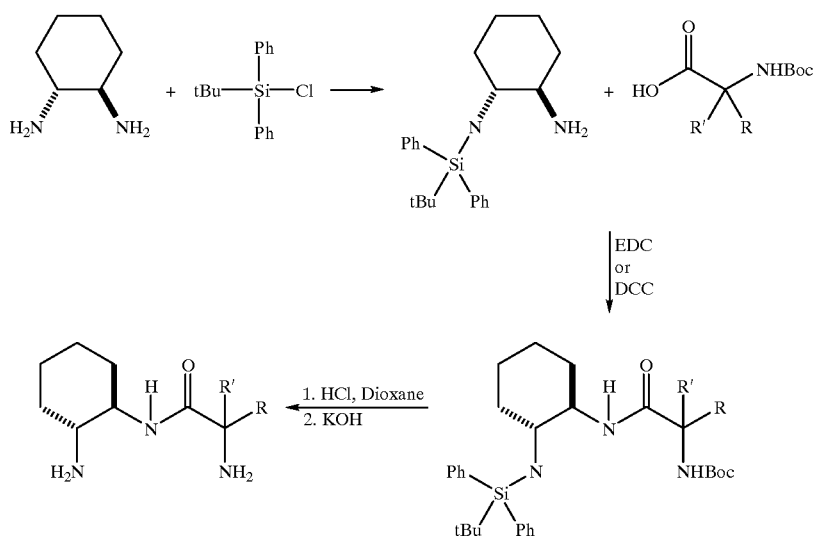
Scheme I
(Bis-1,2-Diaminocyclohexane substitution, β-amino acid chemistry)
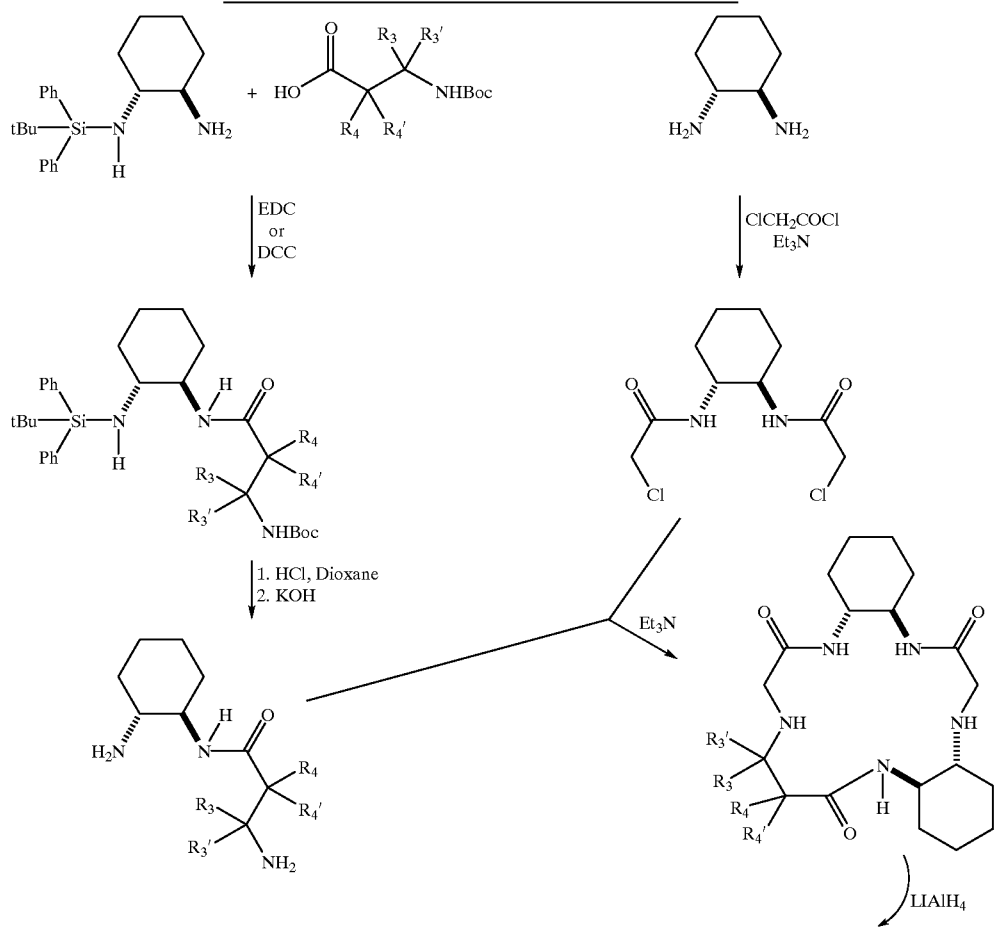

-continued
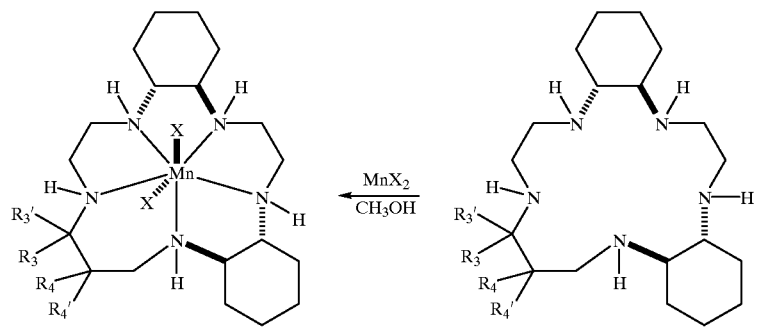
Scheme J
(Bis-1,2-Diaminocyclohexane substitution)
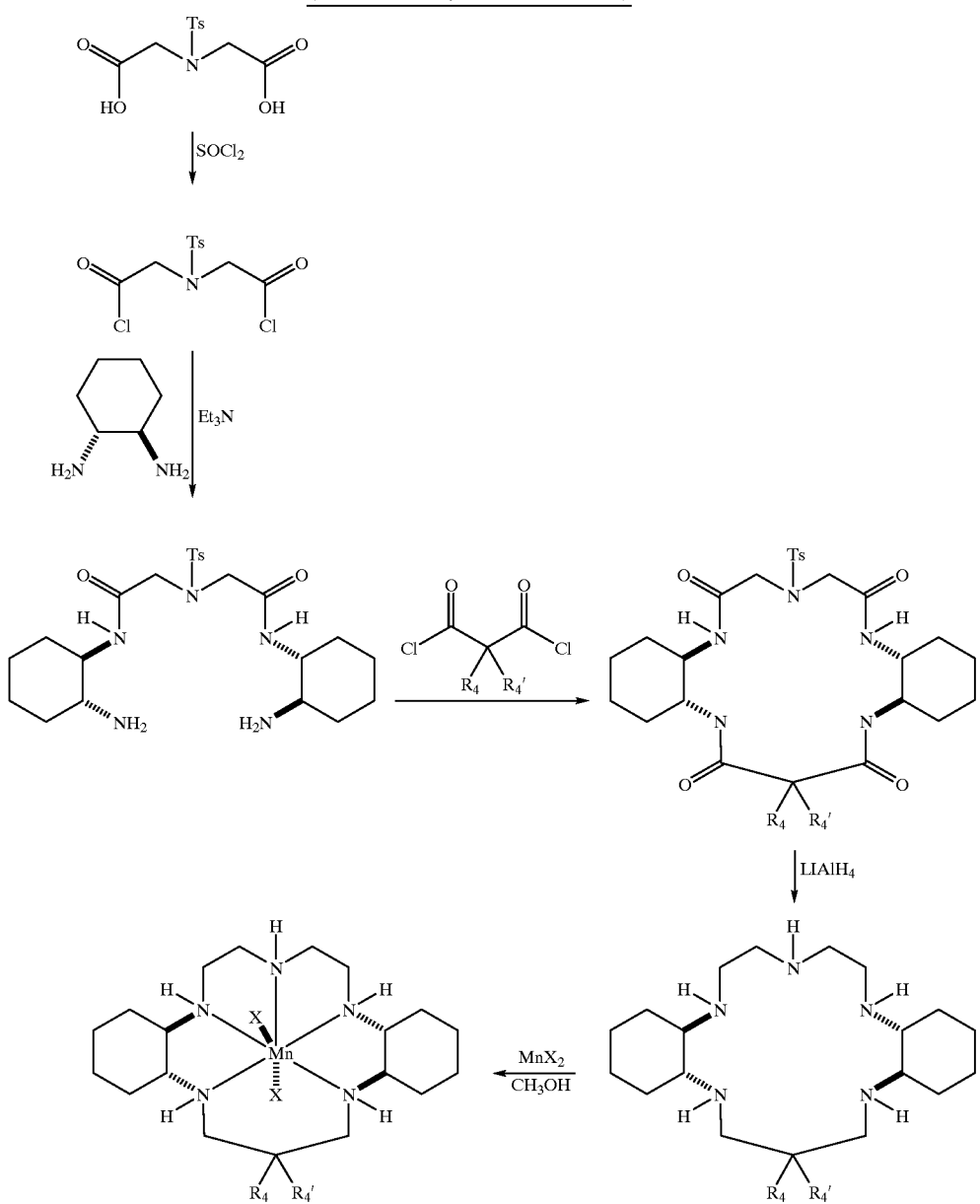

Scheme K
(Cyclic peptide approach with one β-amino acid residue)
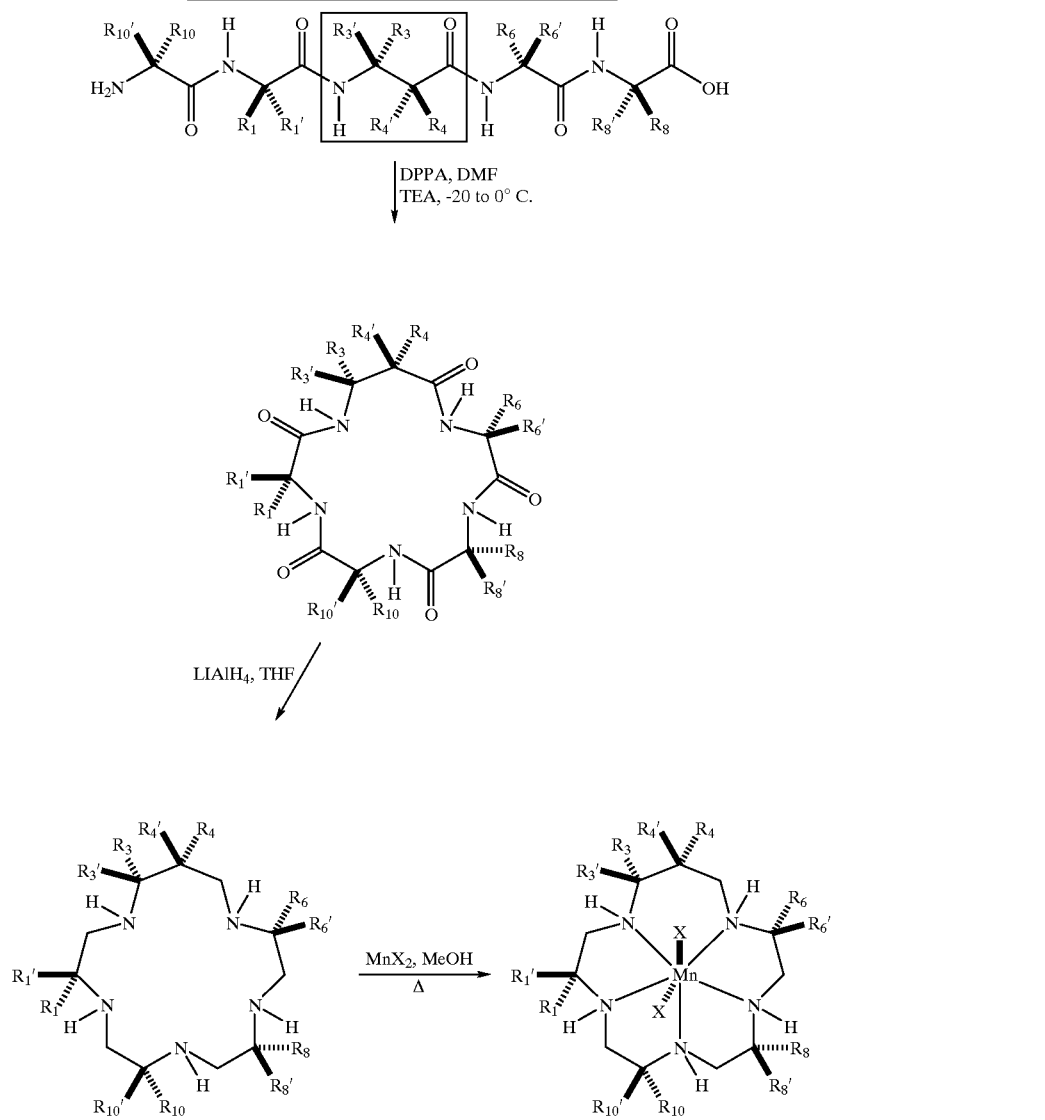
Scheme L
(1,2-diaminocyclohexane pseudo-peptides with β-amino acids)
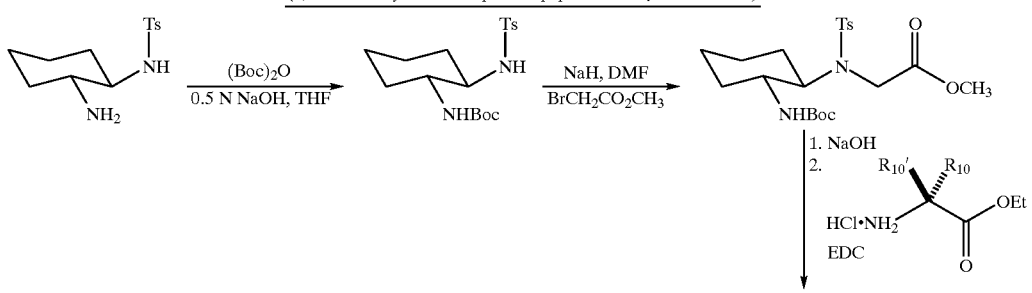

29 30
-continued
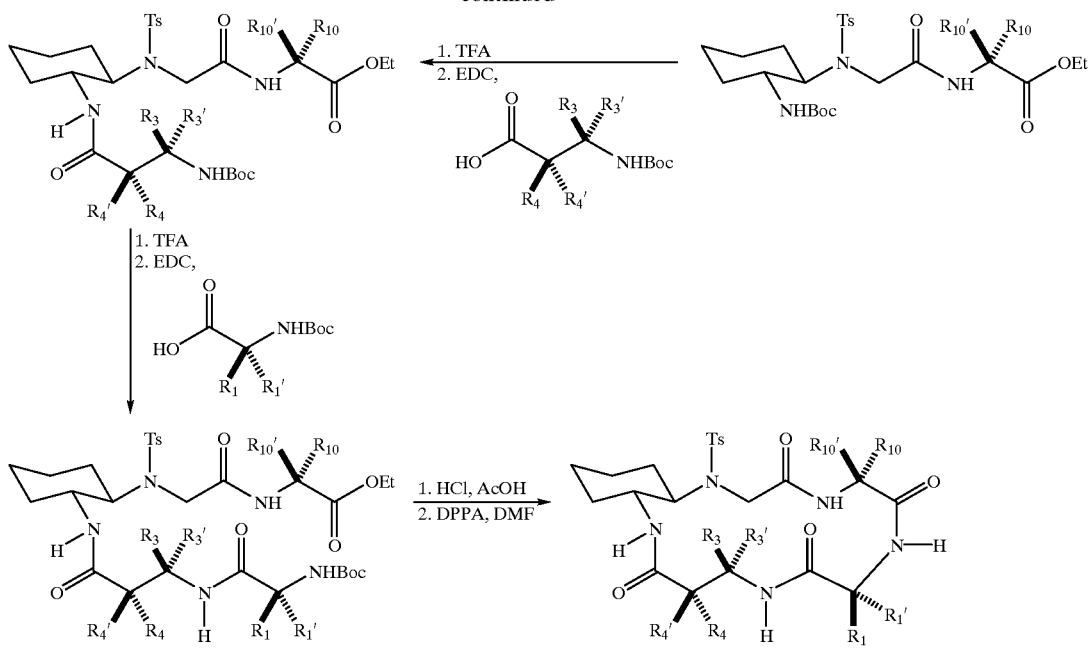
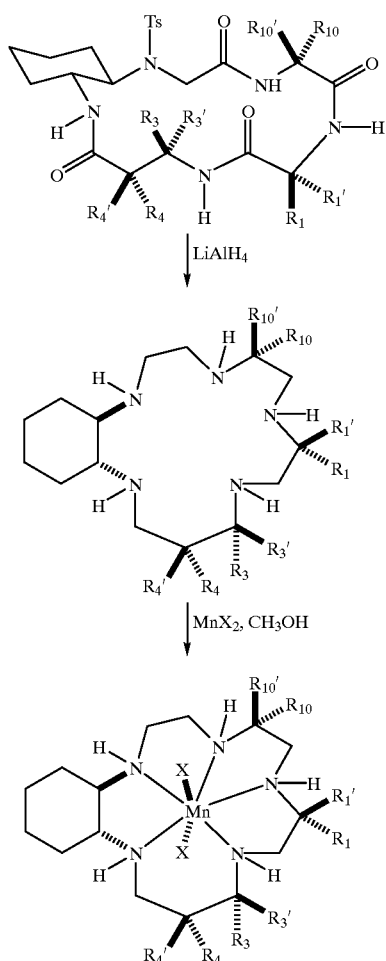

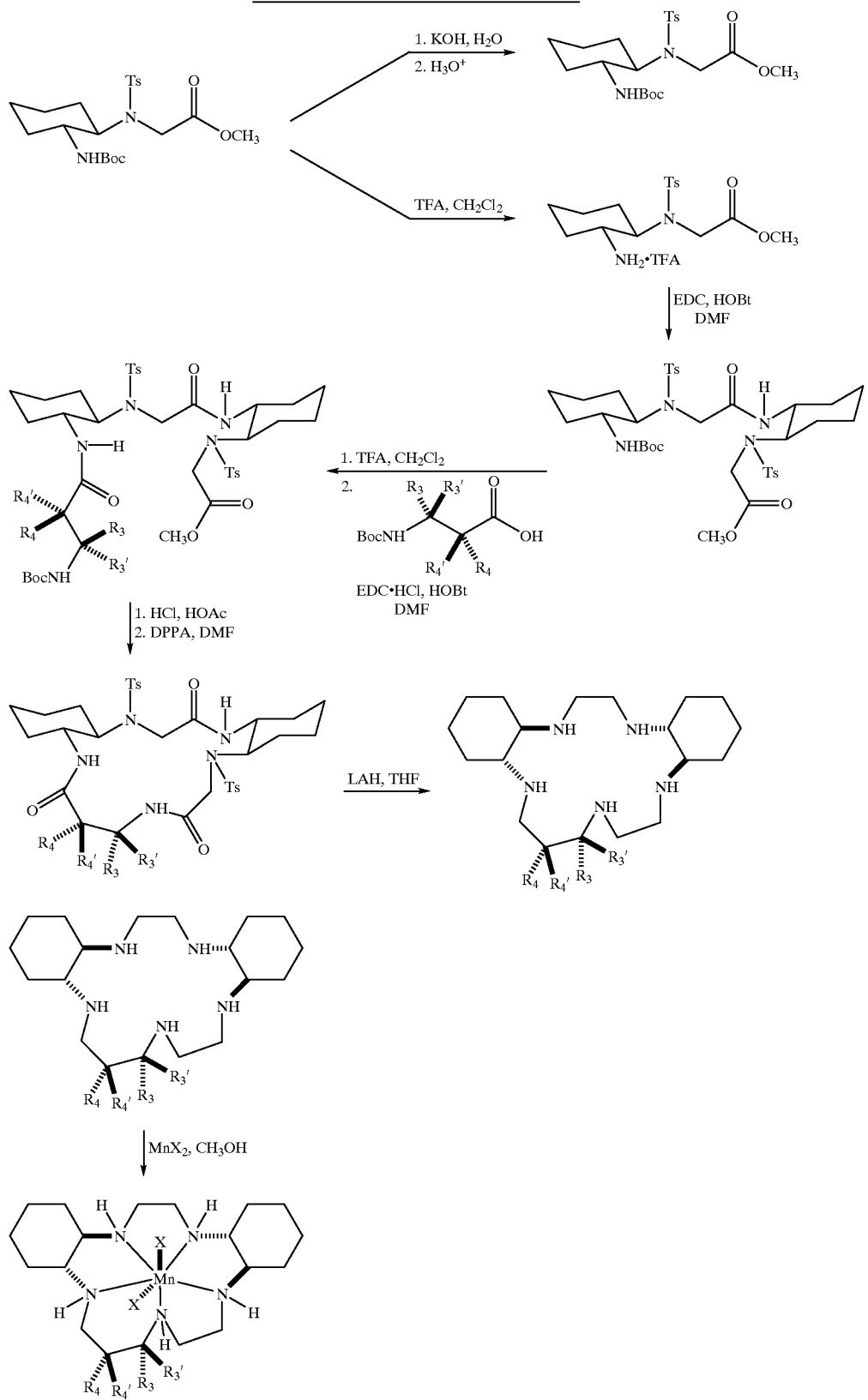

Scheme N
(General 1,3-diaminopropanes with tri-N-tosyl-diacid chloride)
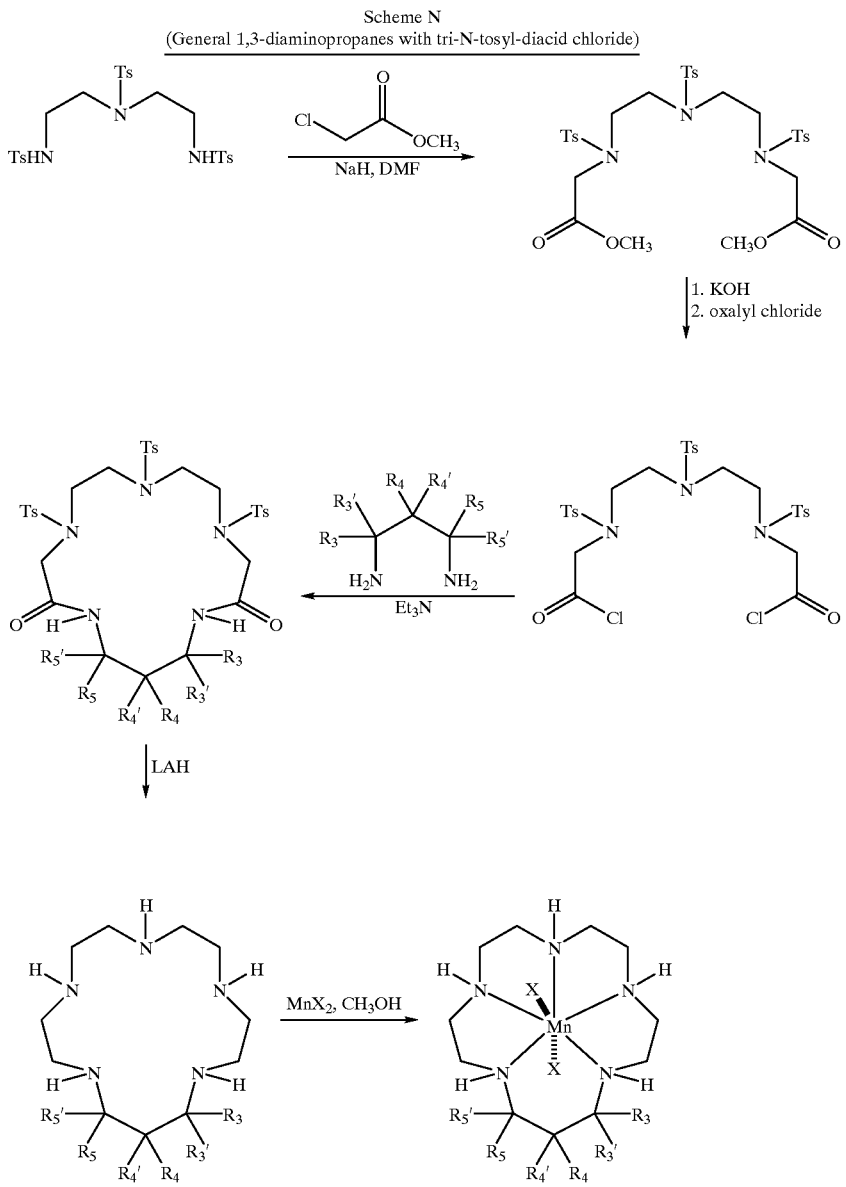
Scheme O
(Aminomethylcyclohexylamines with tri-N-tosyl-diacid chloride)
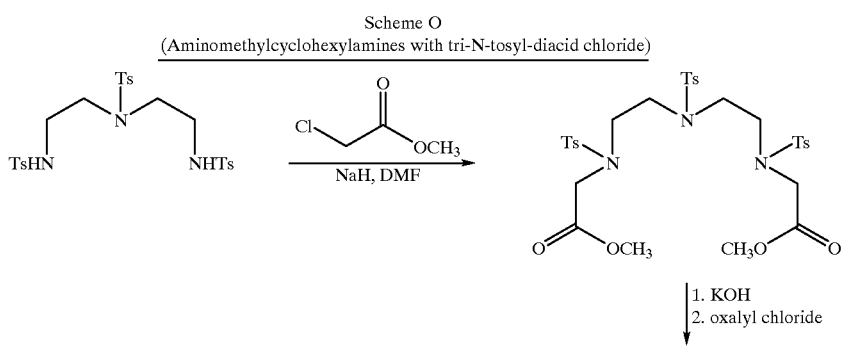

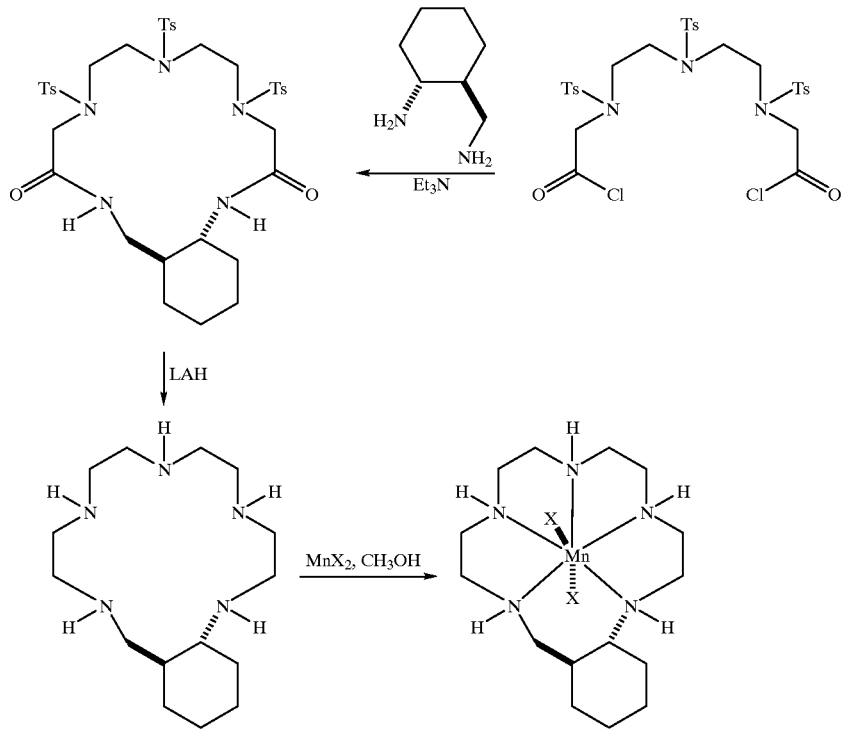
Scheme P
(Aminomethylanilamines with tri-N-tosyl-diacid chloride)
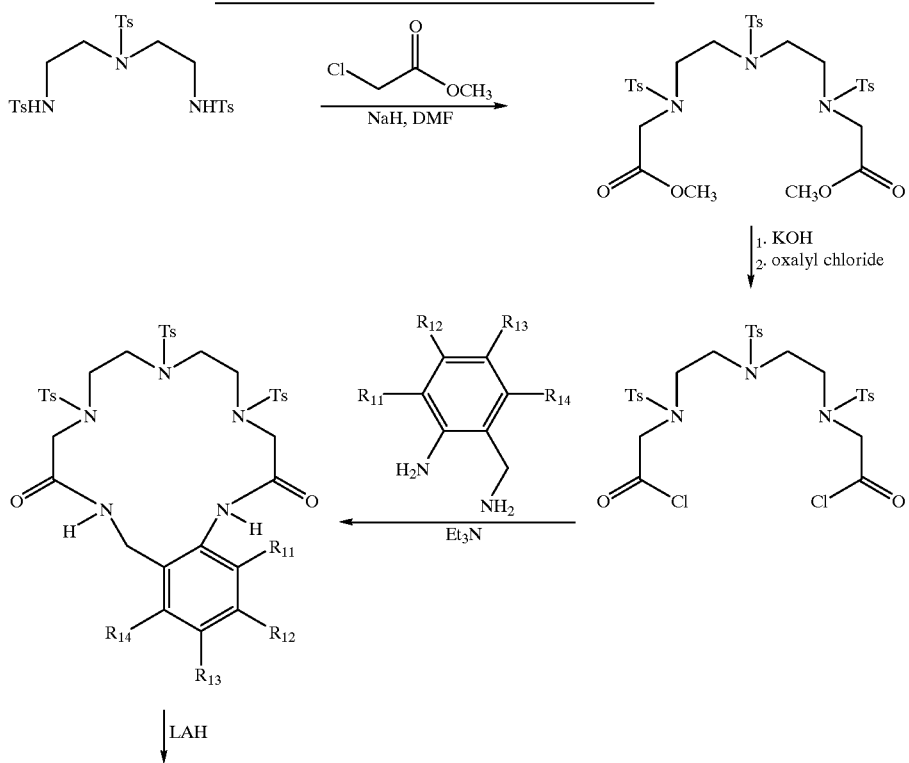

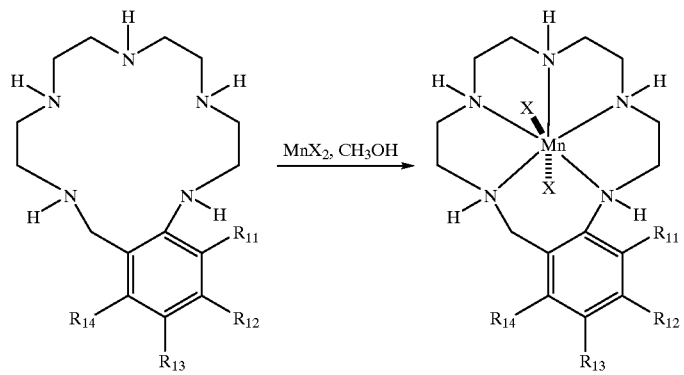

The pentaazamacrocycles of the present invention can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting one or more secondary amine group(s) of the compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure ligand. The optically active compounds of the invention can likewise be obtained by utilizing optically active starting materials, such as natural amino acids.

The compounds or complexes of the present invention are novel and can be utilized to treat numerous inflammatory disease states and disorders. For example, reperfusion injury to an ischemic organ, e.g., reperfusion injury to the ischemic myocardium, myocardial infarction, inflammatory bowel disease, rheumatoid arthritis, osteoarthritis, hypertension, psoriasis, organ transplant rejections, organ preservation, impotence, radiation-induced injury, asthma, atherosclerosis, thrombosis, platelet aggregation, metastasis, influenza, stroke, burns, trauma, acute pancreatitis, pyelonephritis, hepatitis, autoimmune diseases, insulin-dependent diabetes mellitus, disseminated intravascular coagulation, fatty embolism, adult and infantile respiratory distress, carcinogenesis and hemorrhages in neonates.

Activity of the compounds or complexes of the present invention for catalyzing the dismutation of superoxide can be demonstrated using the stopped-flow kinetic analysis technique as described in Riley, D. P., Rivers, W. J. and Weiss, R. H., "Stopped-Flow Kinetic Analysis for Monitoring Superoxide Decay in Aqueous Systems," Anal. Biochem., 196, 344–349 (1991), which is incorporated by reference herein. Stopped-flow kinetic analysis is an accurate and direct method for quantitatively monitoring the decay rates of superoxide in water. The stopped-flow kinetic analysis is suitable for screening compounds for SOD activity and activity of the compounds or complexes of the present invention, as shown by stopped-flow analysis, correlate to treating the above disease states and disorders.

Total daily dose administered to a host in single or divided doses may be in amounts, for example, from about 1 to about 100 mg/kg body weight daily and more usually about 3 to 30 mg/kg. Dosage unit compositions may contain such amounts of submultiples thereof to make up the daily dose.

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, granules and gels. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more compounds which are known to be effective against the specific disease state that one is targeting for treatment.

Contemplated equivalents of the general formulas set forth above for the compounds and derivatives as well as the intermediates are compounds otherwise corresponding thereto and having the same general properties such as tautomers of the compounds and such as wherein one or more of the various R groups are simple variations of the substituents as defined therein, e.g., wherein R is a higher alkyl group than that indicated, or where the tosyl groups are other nitrogen or oxygen protecting groups or wherein the O-tosyl is a halide. Anions having a charge other than 1, e.g., carbonate, phosphate, and hydrogen phosphate, can be used instead of anions having a charge of 1, so long as they do not adversely affect the overall activity of the complex. However, using anions having a charge other than 1 will result in a slight modification of the general formula for the complex set forth above. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure. Further, it is contemplated that manganese(III) complexes will be equivalent to the subject manganese(II) complexes.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

All reagents were used as received without purification unless otherwise indicated. All NMR spectra were obtained on a Varian VXR-300 or VXR-400 nuclear magnetic resonance spectrometer. Qualitative and quantitative mass spectroscopy was run on a Finnigan MAT90, a Finnigan 4500 and a VG40-250T using m-nitrobenzyl alcohol(NBA) or m-nitrobenzyl alcohol/LiCl (NBA+Li). Melting points (mp) are uncorrected.

The following abbreviations relating to amino acids and their protective groups are in accordance with the recommendation by IuPAC-IUB commission on Biochemical Nomenclature (Biochemistry, 11, 1726 (1972)) and common usage.

Ala L-Alanine
DAla D-Alanine
Gly Glycine
ppg Propargylglycine
Tyr L-Tyrosine
Bzl Benzyl
Boo tert-Butoxycarbonyl
Et Ethyl
TFA Trifluoroacetate
DMF Dimethylformamide
HOBT•$H_2O$ 1-Hydroxy-(1H)-benzotriazole monohydrate
EDC•HCl 1-(3-Dimethylaminopropyl)-3-ethylcarbodiimide hydrochloride
TEA Triethylamine
DMSO Dimethylsulfoxide
THF Tetrahydrofuran
DPPA Diphenylphosphoryl azide
DMPU Dimethylpropyleneurea
c concentration, g/cc
DME 1,2-Dimethoxyethane
TsCl Tosyl Chloride
DCC Dicyclohexyl carbodiimide
LAH Lithium aluminum hydride Example 1

A. Synthesis of 1.4.8,11-Tetra(p-toluenesulfonyl)-1,4,8,11-tetraazaundecane

To a stirred solution of p-toluenesulfonyl chloride (262 g, 1.37 mole) in anhydrous pyridine (600 ml) at 5° C. was added a solution of 1,4,8,11-tetraazaundecane (49.1 g, 0.306 mole) in anhydrous pyridine (200 ml) under a dry argon atmosphere, maintaining the temperature <20° C. The addition required 1 h. The mixture was stirred overnight at room temperature. $H_2O$ (1.5 l) was slowly added to the cooled (ice bath) mixture. The resulting oil was dissolved in $CH_2Cl_2$, separated from the aqueous layer. The $CH_2Cl_2$ layer was washed with 5% HCl and $H_2O$ and dried ($MgSO_4$). The solvent was removed in vacuo to give an oil which solidified on standing. The resulting solid was ground to a powder and dried in vacuo to give 186 g (78% yield) of the crude product: $^1H$ NMR ($CDCl_3$) δ 1.98 (quint, J=7.3 Hz, 2 H), 2.40 (s, 6 H), 2.42 (s, 6 H), 3.11 (t, J=7.3 Hz, 4 H), 3.17 (s, 8 H), 5,76 (t, J=6.0 Hz, 2 H), 7.29 (m, 8 H), 7.64 (d, J=8.3 Hz, 4 H), 7.75 (d, J=8.3 Hz, 4 H).

B. Synthesis of 1,4,8,11-Tetra(p-toluenesulfonyl)-1,4,8,11-tetraazaundecane-1.11-disodium Salt To a stirred slurry of 1,4,8,11-tetra(p-toluenesulfonyl)-1, 4,8,11-tetraazaundecane prepared as in Example 11A (80.0 g, 0.103 mole) in ethanol (140 ml) heated to reflux under a dry argon atmosphere was rapidly added a solution of sodium ethoxide (prepared by dissolving sodium metal (5.20 g, 0.227 mole) in ethanol (150 ml)). The brown solution was filtered while hot and the solvent was removed in vacuo to give the crude product as an oily solid: $^1$H NMR (CDCl$_3$) 1.71 (br s, 2 H), 2.26 (s, 6 H), 2.34 (s, 6 H), 2.79 (br m, 4 H), 2.99 (br m, 8 H), 6.90 (d, J=8.1 Hz, 4 H), 7.13 (d, J=8.3 Hz, 4 H), 7.50 (d, J=8.3 Hz, 4 H), 7.57 (d, J=8.1 Hz, 4 H).

C. Synthesis of 3-(p-Toluenesulfonyl)-3-azapentane-1,5-di-p-toluenesulfonate

To a stirred solution of p-toluenesulfonyl chloride (598 g, 3.14 mole) and triethylamine (318 g, 3.14 mole) in anhydrous CH$_2$Cl$_2$ (1.5 l) at 5° C. under a dry argon atmosphere was added a solution of diethanolamine (100 g, 0.951 mole) in anhydrous CH$_2$Cl$_2$ (50 ml) maintaining the temperature <10° C. The addition required 45 minutes. The mixture was allowed to warm to room temperature and was stirred an additional 18 h. H$_2$O (1.5 l) was then added and the CH$_2$Cl$_2$ layer was separated. The CH$_2$Cl$_2$ layer was washed with 10% HCl and H$_2$O and was dried (MgSO$_4$). The solvent was removed in vacuo to give an off-white solid. The crude product was purified by recrystallization from ethyl acetate-hexane to give 329 g (61% yield) of the product as a white powder: mp 86–7.5° C.; $^1$H NMR (CDCl$_3$) δ 2.42 (s, 3 H), 2.46 (s, 6 H), 3.37 (t, J=6.0 Hz, 4 H), 4.11 (t, J=6.0 Hz, 4 H), 7.29 (d, J=7.7 Hz, 2 H), 7.36 (d, J=8.0 Hz, 4 H), 7.62 (d, J=8.4 Hz, 2 H), 7.77 (d, J=8.3 Hz, 4 H).

D. Synthesis of 1,4,7,10,13-Penta(p-toluenesulfonyl)-1,4,7,10,13-pentaazacyclohexadecane To a stirred solution of 1,4,8,11-tetra(p-toluenesulfonyl)-1,4,8,11-tetraazaundecane-1,11-disodium salt prepared as in Example 1B (74.0 g, 0.0901 mole) in anhydrous DMF (800 ml) was added sodium hydride (0.2 g–80% in mineral oil, 6.7 mmol). The unreacted sodium hydride was removed by filtration and the solution was heated to 100° C. under a dry argon atmosphere. To this stirred solution was added a solution of 3-(p-toluenesulfonyl)-3-azapentane-1,5-di-p-toluenesulfonate prepared as in Example 1C (51.2 g, 0.0901 mole) in anhydrous DMF (400 ml) over a 3 h period, maintaining the temperature at 100° C. After stirring the solution an additional 1.25 h at 100° C., the mixture was concentrated in vacuo to a volume of 750 ml. H$_2$0 (2.3 l) was slowly added to crystallize the product. The resulting gummy solid was triturated with ethyl acetate and dried in vacuo to give 31 g (34% yield) of the crude product as a powder: mp 225–300C, $^1$H NMR (CDCl$_3$) δ 1.90 (quint, J=6.0 Hz, 2 H), 2.42 (s, 9 H), 2.44 (s, 6 H), 3.07 (t, J=7.0 Hz, 4 H), 3.15 (m, 4 H), 3.28 (m, 12 H), 7.31 (m, 10 H), 7.67 (m, 10 H).

E. Synthesis of 1,4,7,10,13-Pentaazacyclohexadecane

A mixture of 1,4,7,10,13-penta(p-toluenesulfonyl)-1,4,7,10,13-pentaazacyclohexadecane prepared as in Example 1D (30 g, 0.030 mole) and concentrated H$_2$SO$_4$ (100 ml) was heated at 100° C. with stirring under a dry argon atmosphere for 69 h. To the resulting brown solution, ethanol (200 mL) was added dropwise with stirring at 5° C., followed by ethyl ether (500 ml). The tan solid was filtered and washed thoroughly with ethyl ether. The solid was then dissolved in H$_2$O (75 ml), the pH was adjusted to 10 with 10N NaOH, and the solution was extracted with CHCl$_3$ (6×200 ml). The extracts were combined and dried (Na$_2$SO$_4$), and the solvent was removed in vacuo. The resulting yellow solid was purified by recrystallization from hexane to give 1.0 g (15% yield) of the product as colorless needles: mp 109–110.5° C.; $^1$H NMR (CDCl$_3$)δ 1.72 (quint, J=5.4 Hz, 2 H), 1.76 (br s, 5 H), 2.73 (m, 20 H); Anal. calcd. for C$_{11}$H$_{27}$N$_5$: C, 57.60; H, 11.86; N, 30.53. Found: C, 57.77; H, 12.35; N, 30.57.

F. Synthesis of Manganese(II)dichloro(1,4,7,10,13-pentaazacyclohexadecane)

A solution of 1,4,7,10,13-pentaazacyclohexadecane prepared as in Example 1E (700 mg, 3.1 mmole) and anhydrous manganese(II) chloride (0.38 g, 3.1 mmole) in anhydrous MeOH (50 ml) was refluxed for 2 h under a dry nitrogen atmosphere. After cooling the solvent was removed in vacuo to give a solid. The solid was recrystallized from ethanol-ethyl ether to give 0.81 g (75% yield) of a white crystalline solid: FAB mass spectrum (NBA) m/z (relative intensity) 319/321 [(CM-Cl), $^+$100/29]; C$_{11}$H$_{27}$Cl$_2$MnN$_5$; C, 37.19; H, 7.66; N, 19.72; Cl, 19.96. Found: C, 37.06; H, 7.64; N, 19.94; N, 19.94; Cl, 19.43.

Example 2

Stopped-Flow Kinetic Analysis

Stopped-flow kinetic analysis has been utilized to determine whether a compound can catalyze the dismutation of superoxide (Bull, C., McClune, G. J., and Fee, J. A., (1983) J. Am. Chem. Soc., 105, 5290–5300. For the attainment of consistent and accurate measurements all reagents were biologically clean and metal-free. To achieve this, all buffers (Calbiochem) were biological grade, metal-free buffers and were handled with utensils which had been washed first with 0.1 N HCl, followed by purified water, followed by a rinse in a 10$^{-4}$ M EDTA bath at pH 8, followed by a rinse with purified water and dried at 65° C. for several hours. Dry DMSO solutions of potassium superoxide (Aldrich) were prepared under a dry, inert atmosphere of argon in a Vacuum Atmospheres dry glovebox using dried glassware. The DMSO solutions were prepared immediately before every stopped-flow experiment. A mortar and pestle were used to grind the yellow solid potassium superoxide (~100 mg). The powder was then ground with a few drops of DMSO and the slurry transferred to a flask containing an additional 25 ml of DMSO. The resultant slurry was stirred for ½ h and then filtered. This procedure gave reproducibly ~2 mM concentrations of superoxide in DMSO. These solutions were transferred to a glovebag under nitrogen in sealed vials prior to loading the syringe under nitrogen. It should be noted that the DMSO/superoxide solutions are extremely sensitive to water, heat, air, and extraneous metals. A fresh, pure solution has a very slight yellowish tint.

Water for buffer solutions was delivered from an in-house deionized water system to a Barnstead Nanopure Ultrapure Series 550 water system and then double distilled, first from alkaline potassium permanganate and then from a dilute EDTA solution. For example, a solution containing 1.0 g of potassium permanganate, 2 liters of water and additional sodium hydroxide necessary to bring the pH to 9.0 were added to a 2-liter flask fitted with a solvent distillation head. This distillation will oxidize any trace of organic compounds in the water. The final distillation was carried out under nitrogen in a 2.5-liter flask containing 1500 ml of water from the first still and 1.0×10$^{-6}$M EDTA. This step will remove remaining trace metals from the ultrapure water. To prevent EDTA mist from volatilizing over the reflux arm to the still head, the 40-cm vertical arm was packed with glass beads and wrapped with insulation. This system produces deoxygenated water that can be measured to have a conductivity of less than 2.0 nanomhos/cm$^2$.

The stopped-flow spectrometer system was designed and manufactured by Kinetic Instruments Inc. (Ann Arbor, MI) and was interfaced to a MAC IICX personal computer. The software for the stopped-flow analysis was provided by Kinetics Instrument Inc. and was written in QuickBasic with MacAdios drivers. Typical injector volumes (0.10 ml of buffer and 0.006 ml of DMSO) were calibrated so that a large excess of water over the DMSO solution were mixed together. The actual ratio was approximately 17/1 so that the initial concentration of superoxide in the aqueous solution was in the range 60–120 $\mu$M. Since the published extinction coefficient of superoxide in $H_2O$ at 245 nm is ~2250 $M^{-1}$ $cm^{-1}$ (1), an initial absorbance value of approximately 0.3–0.5 would be expected for a 2-cm path length cell, and this was observed experimentally. Aqueous solutions to be mixed with the DMSO solution of superoxide were prepared using 80 mM concentrations of the Hepes buffer, pH 8.1 (free acid +Na form). One of the reservoir syringes was filled with 5 ml of the DMSO solution while the other was filled with 5 ml of the aqueous buffer solution. The entire injection block, mixer, and spectrometer cell were immersed in a thermostatted circulating water bath with a temperature of 21.0±0.5° C.

Prior to initiating data collection for a superoxide decay, a baseline average was obtained by injecting several shots of the buffer and DMSO solutions into the mixing chamber. These shots were averaged and stored as the baseline. The first shots to be collected during a series of runs were with aqueous solutions that did not contain catalyst. This assures that each series of trials were free of contamination capable of generating first-order superoxide decay profiles. If the decays observed for several shots of the buffer solution were second-order, solutions of manganese(II) complexes could be utilized. In general, the potential SOD catalyst was screened over a wide range of concentrations. Since the initial concentration of superoxide upon mixing the DMSO with the aqueous buffer was ~$1.2 \times 10^{-4}$ M, we wanted to use a manganese (II) complex concentration that was at least 20 times less than the substrate superoxide. Consequently, we generally screened compounds for SOD activity using concentrations ranging from $5 \times 10^{-7}$ to $8 \times 10^{-6}$ M. Data acquired from the experiment was imported into a suitable math program (e.g., Cricket Graph) so that standard kinetic data analyses could be performed. The catalytic rate constant for dismutation of superoxide by the manganese(II) complex of Example 1 was determined from a linear plot of observed rate constant ($k_{obs}$) versus the concentration of the manganese(II) complex. The $k_{obs}$ value was obtained from a linear plot of ln absorbance at 245 nm versus time for the dismutation of superoxide by the manganese(II) complex. The $k_{cat}$ for the manganese(II) complex of Example 1 was found to be $1.1 \times 10^6$ $M^{-1}sec^{-1}$ at pH=8.1 and 21° C. which indicates that the manganese(II) complex of Example 1 is an effective catalyst for the dismutation of superoxide.

What is claimed is:

1. Pharmaceutical composition in unit dosage form useful for dismutating superoxide comprising a therapeutically or prophylactically effective amount of a complex represented by the formula:

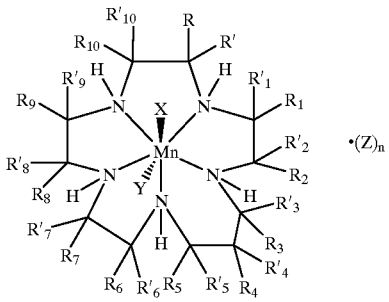

wherein R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$ and $R'_{10}$ independently represents hydrogen, alkyl, alkenyl, alkynyl, cycloalkyl, cycloalkenyl, cycloalkylalkyl, cycloalkylcycloalkyl, cycloalkenylalkyl, alkylcycloalkyl, alkylcycloalkenyl, alkenylcycloalkyl, alkenylcycloalkenyl, heterocyclic, aryl and aralkyl radicals and radicals attached to the α-carbon of α-amino acids or radicals attached to the α-carbon or β-carbon of β-amino acids; $R_1$ or $R_1$ and $R_2$ or $R'_2$, $R_3$ or $R'_3$ and $R_4$ or $R'_4$, $R_3$ or $R'_3$ and $R_5$ or $R'_5$, $R_4$ or $R'_4$ and $R_5$ or $R'_5$, $R_6$ or $R'_6$ and $R_7$ or $R'_7$, $R_8$ or $R'_8$, and $R_9$ or $R'_9$ and $R_{10}$ or $R'_{10}$ and R or R' together with the carbon atoms to which they are attached independently form a saturated, partially saturated or unsaturated cyclic having 3 to 20 carbon atoms; R or R' and $R_1$ or $R'_1$, $R_2$ or $R'_2$ and $R_3$ or $R'_3$ or $R_4$ or $R'_4$, $R_4$ or $R'_4$ or $R_5$ or $R'_5$ and $R_6$ or $R'_6$, $R_7$ or $R'_7$ and $R_8$ or $R'_8$ and $R_9$ or $R'_9$, and $R_{10}$ or $R'_{10}$ together with the carbon atoms to which they are attached independently form a nitrogen containing heterocycle having 2 to 20 carbon atoms provided that when the nitrogen containing heterocycle is an aromatic heterocycle which does not contain a hydrogen attached to the nitrogen, the hydrogen attached to the nitrogen as shown in the above formula, which nitrogen is also in the macrocyclic ligand or complex, and the R groups attached to the same carbon atoms of the macrocycle are absent; R and R', $R_1$ and $R'_1$, $R_2$ and $R'_2$, $R_3$ and $R'_3$, $R_4$ and $R'_4$, $R_5$ and $R'_5$, $R_6$ and $R'_6$, $R_7$ and $R'_7$, $R_8$ and $R'_8$, $R_9$ and $R'_9$, and $R_{10}$ and $R'_{10}$ together with the carbon atom to which they are attached independently form a saturated, partially saturated, or unsaturated ring structure having 3 to 20 carbon atoms; and one of R, R', $R_1$, $R'_1$, $R_2$, $R'_2$, $R_3$, $R'_3$, $R_4$, $R_4$, $R_5$, $R'_5$, $R_6$, $R'_6$, $R_7$, $R'_7$, $R_8$, $R'_8$, $R_9$, $R'_9$, $R_{10}$ and $R'_{10}$ together with a different one of R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$ and $R'_{10}$ which is attached to a different carbon atom in the macrocyclic ligand may be bound to form a strap represented by the formula

wherein w, x, y and z independently are integers from 0 to 10 and M, L and J are independently selected from the group consisting of alkyl, alkenyl, alkynyl, aryl, cycloalkyl, heteroaryl, alkaryl, alkheteroaryl, aza, amide, ammonium, thia, sulfonyl, sulfinyl, sulfonamide, phosphonyl, phosphinyl, phosphino, phosphonium, keto, ester, carbamate, urea, thiocarbonyl, borates, boranes, boraza, silyl, siloxy, silaza and combinations thereof; wherein X, Y and Z are ligands independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof, or X, Y and Z are independently attached to one or more of the "R" groups and n is an integer from 0 to 3; and a nontoxic, pharmaceutically acceptable carrier, adjuvant or vehicle.

2. Composition of claim 1 wherein R is selected from the group consisting of hydrogen and alkyl, cycloalkyl, cycloalkylalkyl, aryl, aralkyl, aminoalkyl and o-hydroxybenzyl radicals and $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, $R'_{10}$ and R' are hydrogen.

3. Composition of claim 2 wherein R is selected from the group consisting of hydrogen and methyl, isobutyl, propargyl, cyclohexylmethyl, benzyl, phenyl, cyclohexyl, 4-benzyloxybenzyl, o-hydroxybenzyl, aminobutyl and octadecyl radicals.

4. Composition of claim 1 wherein X, Y and Z are independently selected from the group consisting of halide, organic acid, nitrate and bicarbonate anions.

5. Method of preventing or treating a disease or disorder which is mediated, at least in part, by superoxide comprising administering to a subject in need of such prevention or treatment, a therapeutically, prophylactically, pathologically, or resuscitative effective amount of a complex of claim 1.

6. Method of claim 5 wherein said disease or disorder is selected from the group consisting of ischemic reperfusion injury, myocardial infarction, metastasis, hypertension, surgically-induced ischemia, inflammatory bowel disease, rheumatoid arthritis, atherosclerosis, thrombosis, platelet aggregation, oxidant-induced tissue injuries and damage, osteoarthritis, psoriasis, organ transplant rejections, impotence, radiation-induced injury, asthma, influenza, stroke, burns, trauma, acute pancreatitis, pyelonephritis, hepatitis, autoimmune diseases, insulin-dependent diabetes mellitus, disseminated intravascular coagulation, fatty embolism, adult and infantile respiratory distress, carcinogenesis and hemorrhages in neonates.

7. Method of using a composition of claim 1 comprising administering said composition to a subject in need of prevention or treatment of a disease or disorder which is mediated at least in part by superoxide or oxygen radicals derived therefrom.

* * * * *